US009526244B2

(12) United States Patent
Satchivi et al.

(10) Patent No.: US 9,526,244 B2
(45) Date of Patent: Dec. 27, 2016

(54) SAFENED HERBICIDAL COMPOSITIONS COMPRISING PYRIDINE CARBOXYLIC ACIDS

(71) Applicant: Dow AgroSciences LLC, Indianapolis, IN (US)

(72) Inventors: Norbert M. Satchivi, Carmel, IN (US); Bryston L. Bangel, Camby, IN (US); Paul R. Schmitzer, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/854,172

(22) Filed: Sep. 15, 2015

(65) Prior Publication Data

US 2016/0135455 A1  May 19, 2016

Related U.S. Application Data

(60) Provisional application No. 62/050,697, filed on Sep. 15, 2014, provisional application No. 62/050,702, filed on Sep. 15, 2014.

(51) Int. Cl.
*A01N 43/40* (2006.01)
*A01N 25/32* (2006.01)
*A01N 43/54* (2006.01)

(52) U.S. Cl.
CPC ............. *A01N 43/40* (2013.01); *A01N 43/54* (2013.01)

(58) Field of Classification Search
CPC ...................................................... A01N 43/40
See application file for complete search history.

(56) References Cited

U.S. PATENT DOCUMENTS

| | | | |
|---|---|---|---|
| 6,297,197 B1 | 10/2001 | Fields et al. | |
| 6,784,137 B2 | 8/2004 | Balko et al. | |
| 7,300,907 B2 | 11/2007 | Epp et al. | |
| 7,314,849 B2 | 1/2008 | Balko et al. | |
| 7,498,468 B2 | 3/2009 | Balko et al. | |
| 7,538,214 B2 | 5/2009 | Epp et al. | |
| 7,642,220 B2 | 1/2010 | Epp et al. | |
| 7,863,220 B2 | 1/2011 | Clark et al. | |
| 7,888,287 B2 | 2/2011 | Epp et al. | |
| 8,288,318 B2 | 10/2012 | Epp et al. | |
| 8,426,591 B2 | 4/2013 | Guenthenspberger et al. | |
| 8,536,331 B2 | 9/2013 | Eckelbarger et al. | |
| 8,609,592 B2 | 12/2013 | Guenthenspberger et al. | |
| 8,754,229 B2 | 6/2014 | Epp et al. | |
| 9,179,676 B2 * | 11/2015 | Hoffmann ............ C07D 417/04 | |
| 2003/0114311 A1 | 6/2003 | Balko et al. | |
| 2007/0179059 A1 | 8/2007 | Epp et al. | |
| 2008/0045734 A1 | 2/2008 | Balko et al. | |
| 2008/0234262 A1 | 9/2008 | Zask et al. | |
| 2009/0048109 A1 | 2/2009 | Epp et al. | |
| 2009/0062121 A1 | 3/2009 | Satchivi et al. | |
| 2009/0088322 A1 | 4/2009 | Epp et al. | |
| 2009/0264429 A1 | 10/2009 | Apodaca et al. | |
| 2010/0137137 A1 | 6/2010 | Rosinger et al. | |
| 2010/0179127 A1 | 7/2010 | Floersheim et al. | |
| 2010/0285959 A1 | 11/2010 | Armel et al. | |
| 2011/0136666 A1 | 6/2011 | Whittingham et al. | |
| 2011/0281873 A1 | 11/2011 | Chiang et al. | |
| 2012/0115724 A1 | 5/2012 | Whittingham et al. | |
| 2012/0184435 A1 | 7/2012 | Bristow et al. | |
| 2012/0190549 A1 | 7/2012 | Eckelbarger et al. | |
| 2012/0288492 A1 | 11/2012 | Kuo et al. | |
| 2012/0292905 A1 | 11/2012 | Slot | |
| 2013/0345240 A1 | 12/2013 | Whitten et al. | |
| 2014/0274695 A1 | 9/2014 | Eckelbarger et al. | |
| 2014/0274701 A1 | 9/2014 | Eckelbarger et al. | |
| 2015/0005165 A1 | 1/2015 | Hoffmann et al. | |

FOREIGN PATENT DOCUMENTS

| | | |
|---|---|---|
| CA | 2842830 A1 | 1/2013 |
| WO | 03011853 A1 | 2/2003 |
| WO | 2005063721 A1 | 7/2005 |
| WO | 2006121648 A2 | 11/2006 |
| WO | 2007080382 A1 | 7/2007 |
| WO | 2007082076 A1 | 7/2007 |
| WO | 2007082098 A2 | 7/2007 |
| WO | 2009007751 A2 | 1/2009 |
| WO | 2009023438 A1 | 2/2009 |
| WO | 2009029735 A1 | 3/2009 |
| WO | 2009081112 A2 | 7/2009 |
| WO | 2010060581 A2 | 6/2010 |
| WO | 2010092339 A1 | 8/2010 |
| WO | 2009138712 A3 | 9/2010 |
| WO | 2010125332 A1 | 11/2010 |
| WO | 2011080568 A2 | 7/2011 |
| WO | 2012080187 A1 | 6/2012 |
| WO | 2012149528 A1 | 11/2012 |
| WO | 2013003740 A1 | 1/2013 |
| WO | 2013014165 A1 | 1/2013 |

OTHER PUBLICATIONS

International Search Report and Written Opinion, issued in International Application No. PCT/US15/50203 on Jan. 14, 2016.
International Search Report and Written Opinion, issued in International Application No. PCT/US15/50205 on Jan. 14, 2016.

(Continued)

*Primary Examiner* — John Pak
(74) *Attorney, Agent, or Firm* — Michael J. Terapane; Meunier Carlin & Curfman, LLC

(57) ABSTRACT

Disclosed herein are safened herbicidal compositions comprising (a) a pyridine carboxylic acid herbicide, or an agriculturally acceptable N-oxide, salt or ester thereof, and (b) an azole carboxylate safener, or agriculturally acceptable salt or ester thereof. Also disclosed herein are methods of controlling undesirable vegetation, comprising applying to vegetation or an area adjacent the vegetation or applying in soil or water to control the emergence or growth of vegetation (a) a pyridine carboxylic acid herbicide, or an agriculturally acceptable N-oxide, salt or ester thereof, and (b) an azole carboxylate safener, or agriculturally acceptable salt or ester thereof.

23 Claims, No Drawings

(56) References Cited

OTHER PUBLICATIONS

International Search Report and Written Opinion, issued in International Application No. PCT/US15/50209 on Jan. 14, 2016.
PUBCHEM. Substance Record for SID 172846318. Deposit Date: Mar. 7, 2013. [retrieved on Dec. 1, 2015]. Retrieved from the Internet, <URL:https://pubchem.ncbl.nlm.nih.gov/substance/172846318/version/1#section=Top>. entire document.
International Search Report and Written Opinion issued in related International Application No. PCT/US2015/050122 on Jul. 5, 2016.
International Search Report and Written Opinion of the EP International Searching Authority from International Application No. PCT/EP2012/064519 mailed Sep. 28, 2012.
International Search Report and Written Opinion issued in International Application No. PCT/US2014/024745 on Jul. 7, 2014.
International Search Report and Written Opinion issued in International Application No. PCT/US2014/024749 on Jul. 10, 2014.
International Search Report and Written Opinion issued in International Application No. PCT/US2014/024752 on Jul. 7, 2014.
International Search Report and Written Opinion issued in International Application No. PCT/US2015/050190 on Dec. 29, 2015.
Abell, "Target-Site Directed Herbicide Design in, pest control with enhanced environmental safety 15-37", 1993.
Knight, et al., "Annual Review of Phytopathology", 1997.
Ruegg, et al., "Weed Research", 2006.

* cited by examiner

SAFENED HERBICIDAL COMPOSITIONS COMPRISING PYRIDINE CARBOXYLIC ACIDS

CROSS REFERENCE TO RELATED APPLICATIONS

This application claims benefit of U.S. Provisional Patent Application No. 62/050,697, filed Sep. 15, 2014, and U.S. Provisional Patent Application No. 62/050,702, filed Sep. 15, 2014, which are hereby incorporated herein by reference in their entireties.

FIELD OF THE DISCLOSURE

The disclosure relates to safened herbicidal compositions comprising a pyridine carboxylic acid herbicide, as well as methods of controlling undesirable vegetation using the same.

BACKGROUND

Many recurring problems in agriculture involve controlling the growth of undesirable vegetation that can, for instance, negatively affect the growth of desirable vegetation. To help control undesirable vegetation, researchers have produced a variety of chemicals and chemical formulations effective in controlling such unwanted growth.

In some cases, although a herbicide may be effective in controlling undesirable vegetation, it may also have a phytotoxic effect on a crop and cause injury or even kill the crop. Accordingly, safeners can be provided with the herbicide to limit the phytotoxicity of the herbicidal active ingredient.

SUMMARY OF THE DISCLOSURE

Disclosed herein are safened herbicidal compositions. The safened herbicidal compositions can comprise (a) a pyridine carboxylic acid herbicide or agriculturally acceptable N-oxide, salt, or ester thereof; and (b) an azole carboxylate safener, or an agriculturally acceptable salt or ester thereof. The weight ratio of (a) in grams acid equivalent per hectare (g ae/ha) to (b) in grams active ingredient per hectare (g ai/ha) can be from 65:1 to 1:5 (e.g., from 5:1 to 1:5, or from 2:1 to 1:2).

The pyridine carboxylic acid herbicide can comprise a compound defined by Formula (I)

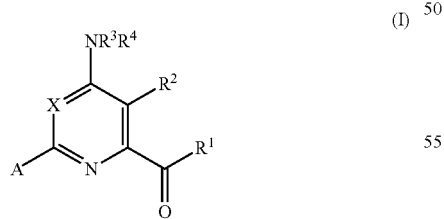

(I)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with $=C$ represent a 5- or 6-membered saturated ring;

A is one of groups A1 to A36

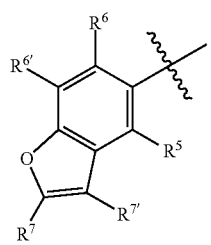

A1

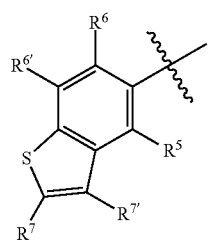

A2

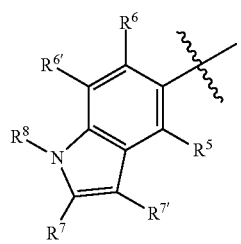

A3

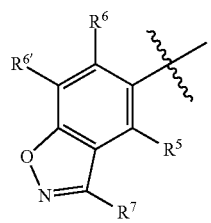

A4

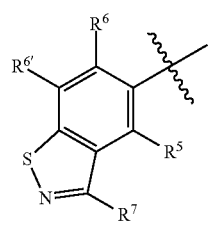
A5
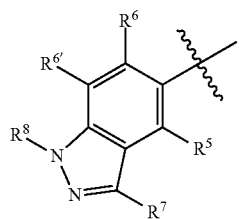
A6
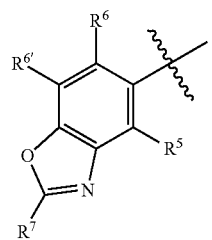
A7
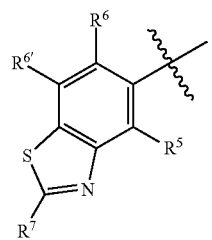
A8
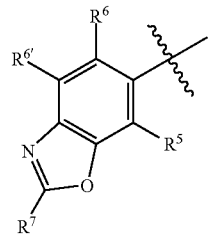
A9
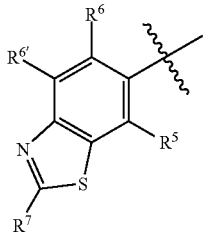
A10
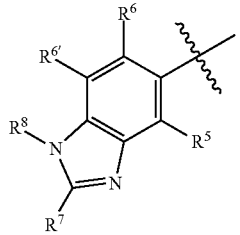
A11
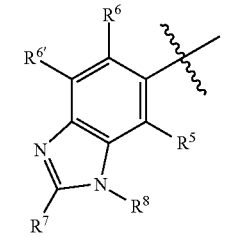
A12
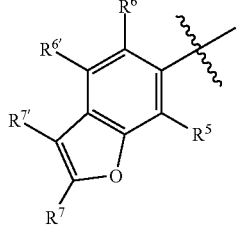
A13
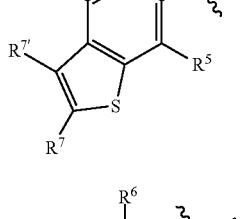
A14
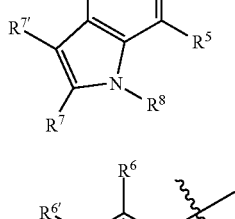
A15
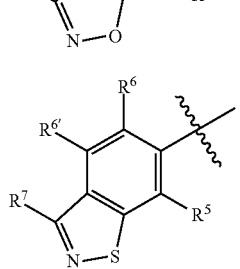
A16
A17

-continued
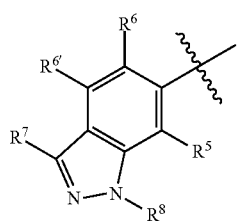 A18
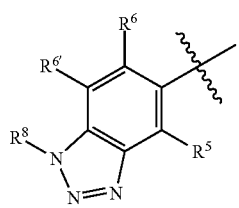 A19
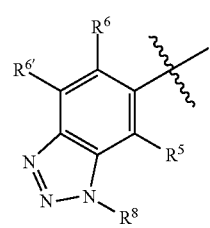 A20
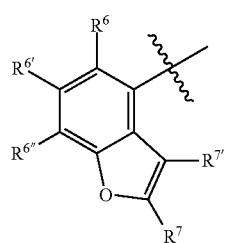 A21
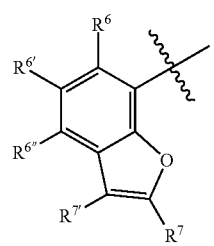 A22
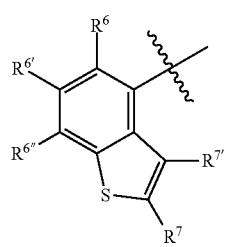 A23
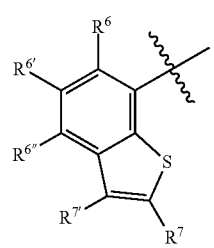 A24
-continued
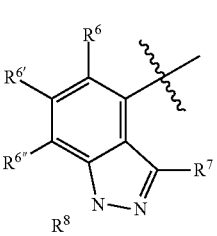 A25
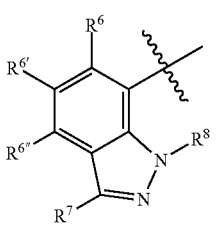 A26
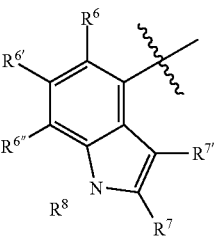 A27
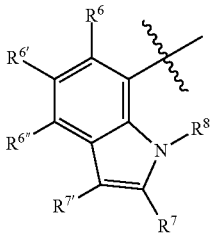 A28
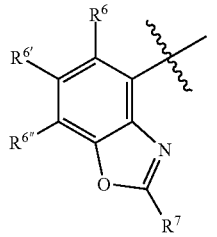 A29
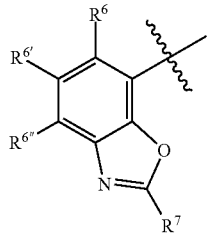 A30

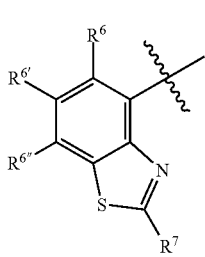

A31

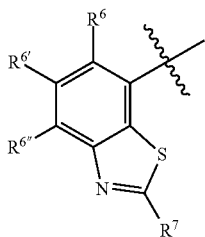

A32

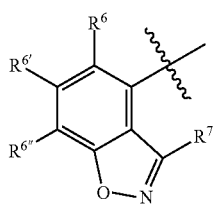

A33

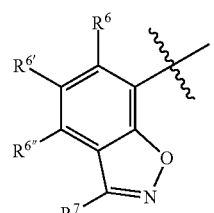

A34

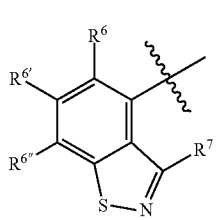

A35

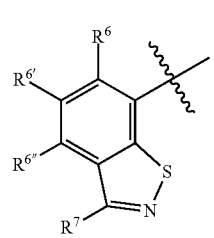

A36

$R^5$, if applicable to the A group, is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$, if applicable to the A group, are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_1$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In certain embodiments, the pyridine carboxylic acid herbicide can comprise a compound defined by Formula (II):

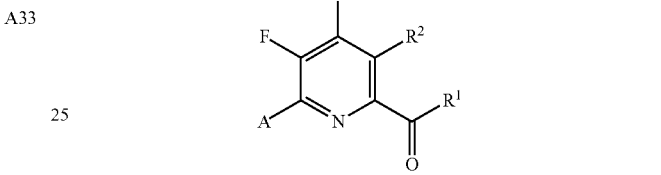

(II)

wherein $R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, $R^1$ is $OR^{1'}$, wherein $R^{1'}$ is hydrogen, $C_1$-$C_8$ alkyl, or $C_7$-$C_{10}$ arylalkyl. In certain embodiments, $R^2$ is Cl, methoxy, vinyl, or 1-propenyl; $R^3$ and $R^4$ are hydrogen; A is A15; $R^5$ is hydrogen or F; $R^6$ is hydrogen or F; and $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can comprise a compound defined by Formula (III):

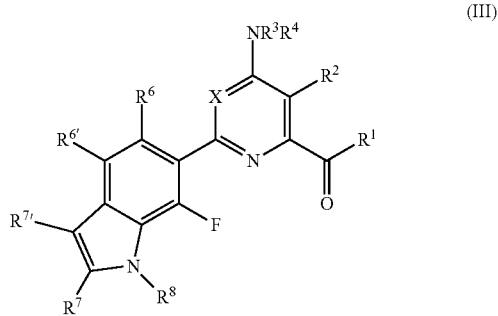

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, X is N, CH or CF. In certain embodiments, X is CF, $R^1$ is $OR^{1'}$, wherein $R^{1'}$ is hydrogen, $C_1$-$C_8$ alkyl, or $C_7$-$C_{10}$ arylalkyl; $R^2$ is Cl, methoxy, vinyl, or 1-propenyl; $R^3$ and $R^4$ are hydrogen; $R^6$ is hydrogen or F; and $R^{6'}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can include 4-amino-3-chloro-5-fluoro-6-(7-fluoro-1H-indol-6-yl) picolinic acid, or an agriculturally acceptable N-oxide, salt, or ester thereof.

In some embodiments, the azole carboxylate safener can be selected from the group consisting of fenchlorazole, isoxadifen, mefenpyr, agriculturally acceptable salts or esters thereof, and combinations thereof.

In some embodiments, the composition can further comprise an agriculturally acceptable adjuvant or carrier, an additional pesticide, or a combination thereof. In certain embodiments, the active ingredients in the composition consist of (a) and (b).

Also disclosed herein are methods of controlling undesirable vegetation, comprising applying to vegetation or an area adjacent the vegetation or applying to soil or water to control the emergence or growth of vegetation (a) a pyridine carboxylic acid herbicide or an agriculturally acceptable N-oxide, salt, or ester thereof and (b) an azole carboxylate safener or an agriculturally acceptable salt or ester thereof. In some embodiments, (a) and (b) are applied simultaneously. In some embodiments, (a) and (b) are applied post-emergence of the undesirable vegetation. In some embodiments, the undesirable vegetation can be controlled in a crop (e.g., in wheat, corn/maize, barley, tame oats, rice, or a combination thereof). In some embodiments, the undesirable vegetation can be controlled in wheat. In some embodiments, the undesirable vegetation can be controlled in corn (e.g., maize).

In some embodiments, (a) can comprise a pyridine carboxylic acid herbicide described above. In some embodiments, the azole carboxylate safener can be selected from the group consisting of fenchlorazole, isoxadifen, mefenpyr, agriculturally acceptable salts or esters thereof, and combinations thereof. In some cases, (a) can be applied in an amount of from 0.1 g ae/ha to 300 g ae/ha (e.g., from 30 g ae/ha to 40 g ae/ha) and/or (b) can be applied in an amount of from 1 g ai/ha to 300 g ai/ha (e.g., from 30 g ai/ha to 40 g ai/ha). In some cases, (a) in g ae/ha and (b) in g ai/ha can be applied in a weight ratio of from 65:1 to 1:5 (e.g., from 5:1 to 1:5, or from 2:1 to 1:2).

The description below sets forth details of one or more embodiment of the present disclosure. Other features, objects, and advantages will be apparent from the description and from the claims.

DETAILED DESCRIPTION

The present disclosure relates to safened herbicidal compositions comprising a herbicidally effective amount of (a) a pyridine carboxylic acid herbicide, or an agriculturally acceptable N-oxide, salt, or ester thereof, and (b) a azole carboxylate safener. The present disclosure also relates to methods for controlling undesirable vegetation. In some embodiments, the undesirable vegetation can be controlled in a crop (e.g., in wheat, corn/maize, barley, tame oats, rice, or a combination thereof). In some embodiments, the undesirable vegetation can be controlled in wheat. In some embodiments, the undesirable vegetation can be controlled in corn (e.g., maize).

I. Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ preceding a group or moiety indicates, in each case, the possible number of carbon atoms in the group or moiety that follows.

As used herein, the terms "herbicide" and "herbicidal active ingredient" refer to an active ingredient that kills, controls, or otherwise adversely modifies the growth of vegetation, particularly undesirable vegetation, such as weeds, when applied in an appropriate amount.

As used herein, a herbicidally effective amount" refers to an amount of an active ingredient that causes a "herbicidal effect," i.e., an adversely modifying effect including, for instance, a deviation from natural growth or development, killing, regulation, desiccation, growth inhibition, growth reduction, and retardation.

As used herein, applying a herbicide or herbicidal composition refers to delivering it directly to the targeted vegetation or to the locus thereof or to the area where control of undesired vegetation is desired. Methods of application include, but are not limited to pre-emergently contacting soil or water, post-emergently contacting the undesirable vegetation or area adjacent to the undesirable vegetation.

As used herein, the terms "crops" and "vegetation" can include, for instance, dormant seeds, germinant seeds, emerging seedlings, plants emerging from vegetative propagules, immature vegetation, and established vegetation.

As used herein, immature vegetation refers to small vegetative plants prior to reproductive stage, and mature vegetation refers to vegetative plants during and after the reproductive stage.

As used herein, the term "acyl" refers to a group of formula —C(O)R, where R is hydrogen, alkyl (e.g., $C_1$-$C_{10}$ alkyl), haloalkyl ($C_1$-$C_8$ haloalkyl), alkenyl ($C_2$-$C_8$ alkenyl), haloalkenyl (e.g., $C_2$-$C_8$ haloalkenyl), alkynyl (e.g., $C_2$-$C_8$ alkynyl), alkoxy ($C_1$-$C_8$ alkoxy), haloalkoxy ($C_1$-$C_8$ alkoxy), aryl, or heteroaryl, arylalkyl ($C_7$-$C_{10}$ arylalkyl), as defined below, where "C(O)" or "CO" is short-hand notation for C=O. In some embodiments, the acyl group can be a $C_1$-$C_6$ acyl group (e.g., a formyl group, a $C_1$-$C_5$ alkylcarbonyl group, or a $C_1$-$C_5$ haloalkylcarbonyl group). In some embodiments, the acyl group can be a $C_1$-$C_3$ acyl group (e.g., a formyl group, a $C_1$-$C_3$ alkylcarbonyl group, or a $C_1$-$C_3$ haloalkylcarbonyl group).

As used herein, the term "alkyl" refers to saturated, straight-chained or branched saturated hydrocarbon moieties. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples of alkyl groups include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl. Alkyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "haloalkyl" refers to straight-chained or branched alkyl groups, wherein these groups the hydrogen atoms may partially or entirely be substituted with halogen atoms. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl, and 1,1,1-trifluoroprop-2-yl. Haloalkyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "alkenyl" refers to unsaturated, straight-chained, or branched hydrocarbon moieties containing a double bond. Unless otherwise specified, $C_2$-$C_{20}$ (e.g., $C_2$-$C_{12}$, $C_2$-$C_{10}$, $C_2$-$C_8$, $C_2$-$C_6$, $C_2$-$C_4$) alkenyl groups are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl- 2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH=CH$_2$; 1-propenyl refers to a group with the structure —CH=CH—CH$_3$; and 2-propenyl refers to a group with the structure —CH$_2$—CH=CH$_2$. Alkenyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

The term "haloalkenyl," as used herein, refers to an alkenyl group, as defined above, which is substituted by one or more halogen atoms.

As used herein, the term "alkynyl" represents straight-chained or branched hydrocarbon moieties containing a triple bond. Unless otherwise specified, $C_2$-$C_{20}$ (e.g., $C_2$-$C_{12}$, $C_2$-$C_{10}$, $C_2$-$C_8$, $C_2$-$C_6$, $C_2$-$C_4$) alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-1-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "alkoxy" refers to a group of the formula R—O—, where R is unsubstituted or substituted alkyl as defined above. Unless otherwise specified, alkoxy groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-dimethyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, the term "haloalkoxy" refers to a group of the formula R—O—, where R is unsubstituted or substituted haloalkyl as defined above. Unless otherwise specified, haloalkoxy groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) haloalkyl group are intended. Examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, and 1,1,1-trifluoroprop-2-oxy.

As used herein, the term "alkylthio" refers to a group of the formula R—S—, where R is unsubstituted or substituted alkyl as defined above. Unless otherwise specified, alkylthio groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethyl-propylthio, 1-ethyl-1-methylpropylthio, and 1-ethyl-2-methylpropylthio.

As used herein, the term "haloalkylthio" refers to an alkylthio group as defined above wherein the carbon atoms are partially or entirely substituted with halogen atoms. Unless otherwise specified, haloalkylthio groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio, and 1,1,1-trifluoroprop-2-ylthio.

As used herein, the term "aryl," as well as derivative terms such as aryloxy, refers to groups that include a monovalent aromatic carbocyclic group of from 6 to 14 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphthyl, phenylcyclopropyl, and indanyl. In some embodiments, the aryl group can be a phenyl, indanyl or naphthyl group. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more chemical moieties. Examples of suitable substituents include, for example, hydroxy, halogen, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_6$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_2$ alkyl and $C_1$-$C_2$ haloalkyl.

As used herein, the term "alkylcarbonyl" refers to an unsubstituted or substituted alkyl group bonded to a carbonyl group. $C_1$-$C_3$ alkylcarbonyl and $C_1$-$C_3$ haloalkylcarbonyl refer to groups wherein a $C_1$-$C_3$ unsubstituted or substituted alkyl or haloalkyl group is bonded to a carbonyl group (the group contains a total of 2 to 4 carbon atoms).

As used herein, the term "alkoxycarbonyl" refers to a group of the formula

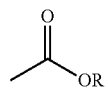

wherein R is unsubstituted or substituted alkyl.

As used herein, the term "arylalkyl" refers to an alkyl group substituted with an unsubstituted or substituted aryl group. $C_7$-$C_{10}$ arylalkyl refers to a group wherein the total number of carbon atoms in the group is 7 to 10, not including the carbon atoms present in any substituents of the aryl group.

As used herein, the term "alkylamino" refers to an amino group substituted with one or two unsubstituted or substituted alkyl groups, which may be the same or different.

As used herein, the term "haloalkylamino" refers to an alkylamino group wherein the alkyl carbon atoms are partially or entirely substituted with halogen atoms.

As used herein, $C_1$-$C_6$ alkylaminocarbonyl refers to a group of the formula RNHC(O)— wherein R is $C_1$-$C_6$ unsubstituted or substituted alkyl, and $C_1$-$C_6$ dialkylaminocarbonyl refers to a group of the formula $R_2NC(O)$— wherein each R is independently $C_1$-$C_6$ unsubstituted or substituted alkyl.

As used herein, the term "alkylcarbamyl" refers to a carbamyl group substituted on the nitrogen with an unsubstituted or substituted alkyl group.

As used herein, the term "alkylsulfonyl" refers to a group of the formula

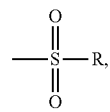

where R is unsubstituted or substituted alkyl.

As used herein, the term "carbamyl" (also referred to as carbamoyl and aminocarbonyl) refers to a group of the formula

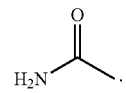

As used herein, the term "dialkylphosphonyl" refers to a group of the formula

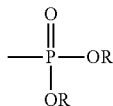

where R is independently unsubstituted or substituted alkyl in each occurrence.

As used herein, $C_1$-$C_6$ trialkylsilyl refers to a group of the formula —$SiR_3$ wherein each R is independently a $C_1$-$C_6$ unsubstituted or substituted alkyl group (the group contains a total of 3 to 18 carbon atoms).

As used herein, Me refers to a methyl group; OMe refers to a methoxy group; and i-Pr refers to an isopropyl group.

As used herein, the term "halogen" including derivative terms such as "halo" refers to fluorine, chlorine, bromine and iodine.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Compounds described herein can include N-oxides. Pyridine N-oxides can be obtained by oxidation of the corresponding pyridines. Suitable oxidation methods are described, for example, in Houben-Weyl, *Methoden der organischen Chemie [Methods in organic chemistry]*, expanded and subsequent volumes to the 4th edition, volume E 7b, p. 565 f.

Pyridine Carboxylic Acid Herbicides

Compositions and methods of the present disclosure can include a pyridine carboxylic acid herbicide defined by Formula (I)

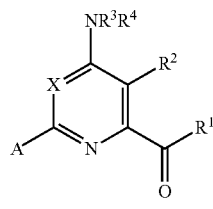
(I)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with $=C$ represent a 5- or 6-membered saturated ring;

A is one of groups A1 to A36

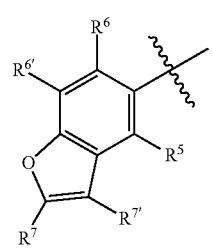
A1

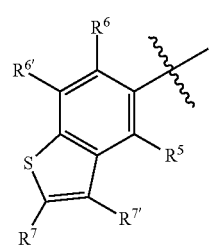
A2

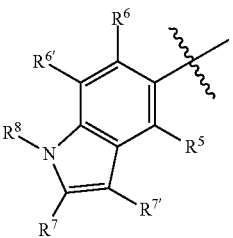
A3

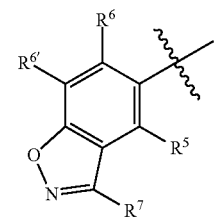
A4

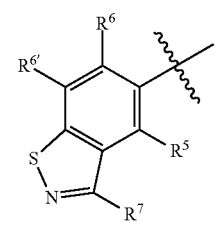
A5

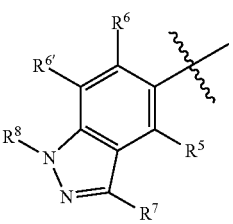
A6

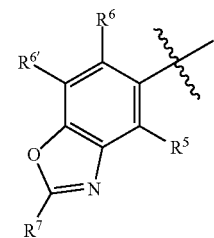
A7

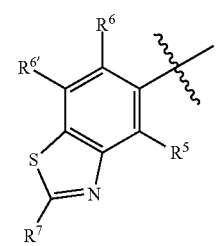
A8

-continued
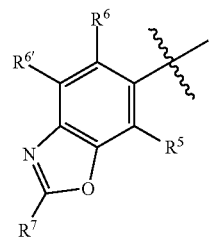 A9
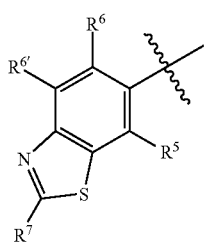 A10
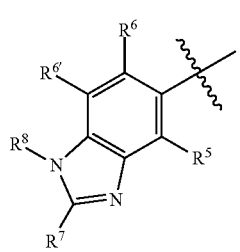 A11
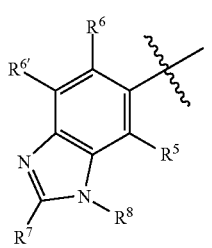 A12
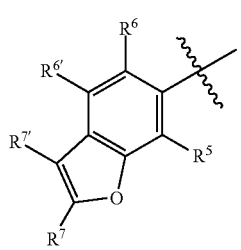 A13
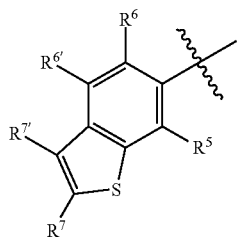 A14
-continued
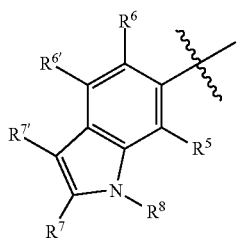 A15
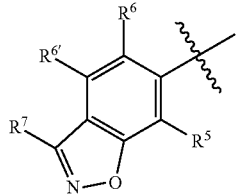 A16
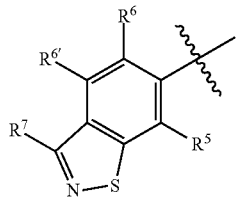 A17
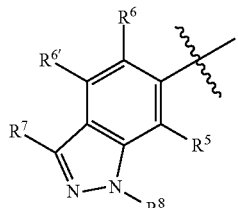 A18
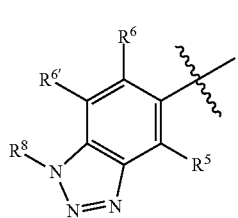 A19
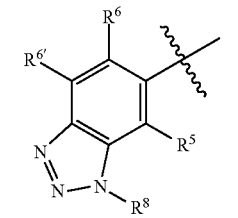 A20
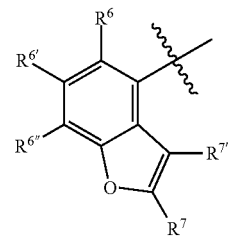 A21

| | |
|---|---|
| 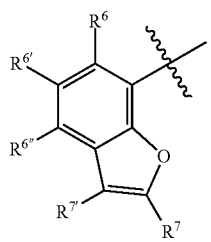 A22 | 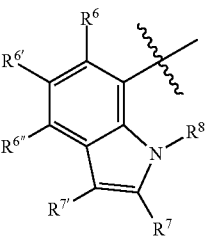 A28 |
| 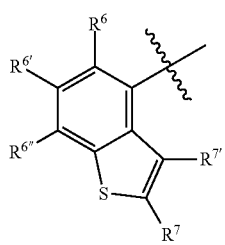 A23 | 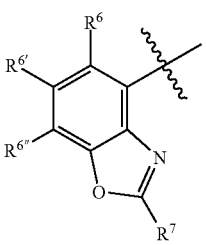 A29 |
| 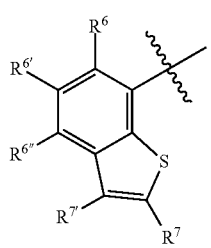 A24 | 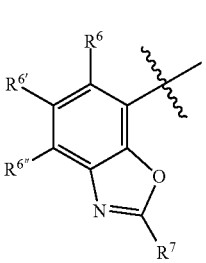 A30 |
| 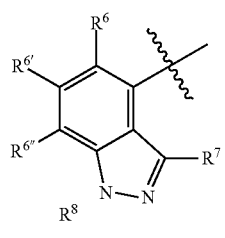 A25 | 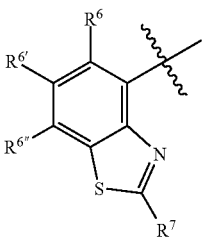 A31 |
| 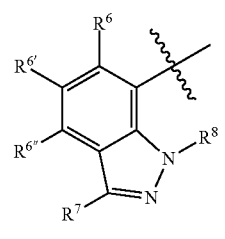 A26 | 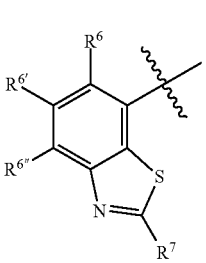 A32 |
| 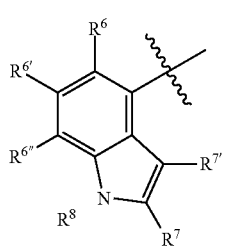 A27 | 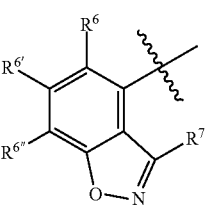 A33 |

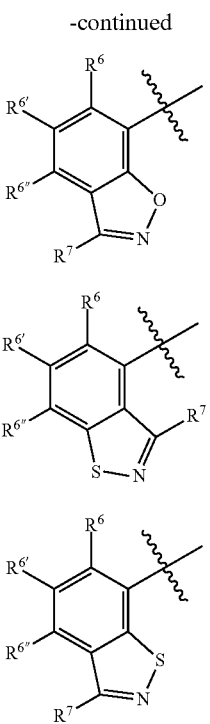

A34

A35

A36

$R^5$, if applicable to the A group, is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$, if applicable to the A group, are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_1$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, $R^1$ is $OR^{1'}$, wherein $R^{1'}$ is hydrogen, $C_1$-$C_8$ alkyl, or $C_7$-$C_{10}$ arylalkyl. In some embodiments, $R^{1'}$ is hydrogen or $C_1$-$C_8$ alkyl. In some embodiments, $R^{1'}$ is hydrogen.

In some embodiments, $R^2$ is halogen, $C_1$-$C_4$ alkyl, $C_1$-$C_4$ haloalkyl, $C_2$-$C_4$ alkynyl, $C_2$-$C_4$-alkenyl, $C_2$-$C_4$ haloalkenyl, $C_1$-$C_4$-alkoxy, or $C_1$-$C_4$ haloalkoxy. In some embodiments, $R^2$ is halogen, $C_2$-$C_4$-alkenyl, $C_2$-$C_4$ haloalkenyl, or $C_1$-$C_4$-alkoxy. In some embodiments, $R^2$ is halogen. In some embodiments, $R^2$ is $C_2$-$C_4$-alkenyl or $C_2$-$C_4$ haloalkenyl. In some embodiments, $R^2$ is $C_1$-$C_4$ alkoxy. In some embodiments, $R^2$ is Cl, OMe, vinyl, or 1-propenyl. In some embodiments, $R^2$ is Cl. In some embodiments, $R^2$ is OMe. In some embodiments, $R^2$ is vinyl or 1-propenyl.

In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy, or $C_1$-$C_6$ alkylamino. In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, or $R^3$ and $R^4$ taken together represent $=CR^{3'}(R^{4'})$, wherein $R^{3'}$ and $R^{4'}$ are independently hydrogen, $C_1$-$C_6$ alkyl, $C_1$-$C_6$ alkoxy or $C_1$-$C_6$ alkylamino. In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, formyl, $C_1$-$C_3$ alkylcarbonyl, or $C_1$-$C_3$ haloalkylcarbonyl. In some embodiments, at least one of $R^3$ and $R^4$ are hydrogen. In some embodiments, $R^3$ and $R^4$ are both hydrogen.

In some embodiments, X is N, CH or CF. In some embodiments, X is N. In some embodiments, X is CH. In some embodiments, X is CF. In other embodiments, X is C—$CH_3$.

In some embodiments, A is A1, A2, A3, A4, A5, A6, A7, A8, A9, A10, A11, A12, A13, A14, A15, A16, A17, A18, A19, or A20. In other embodiments, A is one of A21, A22, A23, A24, A25, A26, A27, A28, A29, A30, A31, A32, A33, A34, A35, and A36.

In some embodiments, A is one of groups A1, A2, A3, A7, A8, A9, A10, A13, A14, and A15. In some embodiments, A is one of groups A1, A2, A3, A13, A14, and A15. In some embodiments, A is one of groups A13, A14, and A15. In some embodiments, A is A15.

In some embodiments, $R^5$ is hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, or amino. In some embodiments, $R^5$ is hydrogen, halogen, $C_1$-$C_4$ alkyl, $C_1$-$C_4$ haloalkyl, $C_1$-$C_3$ alkoxy, $C_1$-$C_3$ haloalkoxy, or amino. In some embodiments, $R^5$ is hydrogen, halogen, $C_1$-$C_4$ alkyl or $C_1$-$C_4$ alkoxy. In some embodiments, $R^5$ is hydrogen or F. In some embodiments, $R^5$ is hydrogen.

In other embodiments, $R^5$ is F.

In some embodiments, $R^6$ is hydrogen, halogen, $C_1$-$C_4$ alkyl, $C_1$-$C_4$ haloalkyl, $C_1$-$C_3$ alkoxy, or $C_1$-$C_3$ haloalkoxy. In some embodiments, $R^6$ is hydrogen or fluorine. In some embodiments, $R^6$ is hydrogen. In some embodiments, $R^6$ is fluorine.

In some embodiments, $R^{6'}$ is hydrogen or halogen. In some embodiments, $R^{6'}$ is hydrogen, F, or Cl. In some embodiments, $R^{6'}$ is hydrogen or F. In some embodiments, $R^{6'}$ is hydrogen.

In some embodiments, $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$. In some embodiments, $R^{6''}$ is hydrogen. In some embodiments, $R^{6''}$ is halogen. In some embodiments, $R^{6''}$ is $C_1$-$C_4$ alkyl. In some embodiments, $R^{6''}$ is $C_1$-$C_4$ haloalkyl. In some embodiments, $R^{6''}$ is cyclopropyl. In some embodiments, $R^{6''}$ is $C_2$-$C_4$ alkynyl. In some embodiments, $R^{6''}$ is CN. In some embodiments, $R^{6''}$ is $NO_2$.

In some embodiments:

X is N, CH, CF, CCl, or CBr;

$R^1$ is $OR^{1'}$, wherein $R^{1'}$ is hydrogen or $C_1$-$C_4$ alkyl;

$R^2$ is chlorine;

$R^3$ and $R^4$ are hydrogen;

A is A1, A2, A3, A4, A5, A6, A7, A8, A9, A10, A11, A12, A13, A14, A15, A16, A17, A18, A19, or A20;

R⁵ is hydrogen, halogen, OH, amino, CN, C₁-C₃ alkyl, C₁-C₃ alkoxy, C₁-C₃ alkylamino, or cyclopropyl;

R⁶, R⁶', and R⁶'' are independently hydrogen, halogen, OH, NH₂, CN, C₁-C₃ alkyl, C₁-C₃ alkoxy, cyclopropyl, or vinyl;

R⁷ and R⁷' are independently hydrogen, halogen, C₁-C₃ alkyl, C₁-C₃ alkoxy, C₁-C₃ alkylthio, cyclopropyl, C₁-C₃ alkylamino, or phenyl; and R⁸ is hydrogen, C₁-C₃ alkyl, phenyl, or C₁-C₃ alkylcarbonyl.

In some embodiments, R² is halogen, C₂-C₄-alkenyl, C₂-C₄ haloalkenyl, or C₁-C₄ alkoxy; R³ and R⁴ are both hydrogen; and X is N, CH, or CF.

In some embodiments, R² is halogen; R³ and R⁴ are both hydrogen; and X is N, CH, or CF.

In some embodiments, R² is C₂-C₄-alkenyl or C₂-C₄ haloalkenyl; R³ and R⁴ are both hydrogen; and X is N, CH, or CF.

In some embodiments, R² is C₁-C₄-alkoxy; R³ and R⁴ are both hydrogen; and X is N, CH, or CF.

In some embodiments, R² is halogen, C₂-C₄-alkenyl, C₂-C₄ haloalkenyl, or C₁-C₄ alkoxy; R³ and R⁴ are both hydrogen; X is N, CH, or CF; R⁵ is hydrogen or F; R⁶ is hydrogen or F; R⁶' is hydrogen; R⁶'', if applicable to the relevant A group, is hydrogen or halogen; and R⁷ and R⁷', if applicable to the relevant A group, are independently hydrogen or halogen.

In some embodiments, R² is halogen, C₁-C₄-alkoxy, or C₂-C₄-alkenyl; R³ and R⁴ are hydrogen; X is N, CH, or CF; and A is one of groups A1 to A20.

In some embodiments, R² is chlorine; R³ and R⁴ are hydrogen; X is N, CH, or CF; A is one of groups A1 to A20; R⁵ is hydrogen or F; R⁶ and R⁶' are independently hydrogen or F; and R⁷ and R⁷', if applicable to the relevant A group, are independently hydrogen, halogen, C₁-C₄ alkyl, or C₁-C₄ haloalkyl.

In some embodiments, R² is chlorine, methoxy, vinyl, or 1-propenyl; R³ and R⁴ are hydrogen; and X is N, CH, or CF.

In some embodiments, R² is chlorine; R³ and R⁴ are hydrogen; and X is N, CH, or CF.

In some embodiments, R² is vinyl or 1-propenyl; R³ and R⁴ are hydrogen; and X is N, CH, or CF.

In some embodiments, R² is methoxy; R³ and R⁴ are hydrogen; and X is N, CH, or CF.

In some embodiments, R² is chlorine; R³ and R⁴ are hydrogen; and X is N.

In some embodiments, R² is chlorine; R³ and R⁴ are hydrogen; and X is CH.

In some embodiments, R² is chlorine; R³ and R⁴ are hydrogen; and X is CF.

In some embodiments, R² is chlorine; R³ and R⁴ are hydrogen; X is CF; A is one of A1, A2, A3, A7, A8, A9, A10, A13, A14, or A15; R⁵ is F; and R⁶ is H.

In some embodiments, R² is chlorine, methoxy, vinyl, or 1-propenyl; R³ and R⁴ are hydrogen; X is N, CH, or CF; and A is one of A21 to A36.

In some embodiments, R² is chlorine, methoxy, vinyl, or 1-propenyl; R³ and R⁴ are hydrogen; X is CF; and A is one of wherein R⁵ is hydrogen or F.

In some embodiments, R² is chlorine, methoxy, vinyl, or 1-propenyl; R³ and R⁴ are hydrogen; X is N, CH, or CF; and A is where R⁵ is hydrogen or F.

In some embodiments, R² is chlorine, methoxy, vinyl, or 1-propenyl; R³ and R⁴ are hydrogen; X is N, CH, or CF; and A is In some embodiments, R² is chlorine, methoxy, vinyl, or 1-propenyl; R³ and R⁴ are hydrogen; X is CF; and A is

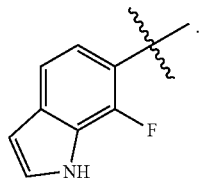 [SMILES: *c1ccc2cc[nH]c2c1F]

In some embodiments, the pyridine carboxylic acid herbicide can comprise a compound defined by Formula (I)

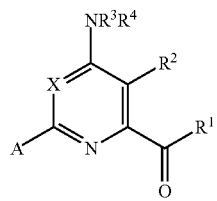

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, CN, or $NO_2$;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof, with the proviso that the pyridine carboxylic acid herbicide is not a compound defined by Formula (I)

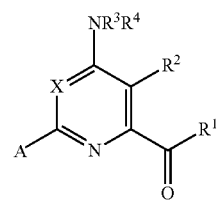

wherein

X is N, CH, CF, CCl, or CBr;

$R^1$ is $OR^{1'}$, wherein $R^{1'}$ is hydrogen or $C_1$-$C_4$ alkyl;

$R^2$ is chlorine;

$R^3$ and $R^4$ are hydrogen;

A is A1, A2, A3, A4, A5, A6, A7, A8, A9, A10, A11, A12, A13, A14, A15, A16, A17, A18, A19, or A20;

$R^5$ is hydrogen, halogen, OH, amino, CN, $C_1$-$C_3$ alkyl, $C_1$-$C_3$ alkoxy, $C_1$-$C_3$ alkylamino, or cyclopropyl;

$R^6$, $R^{6'}$, and $R^{6''}$ are independently hydrogen, halogen, OH, $NH_2$, CN, $C_1$-$C_3$ alkyl, $C_1$-$C_3$ alkoxy, cyclopropyl, or vinyl;

$R^7$ and $R^{7'}$ are independently hydrogen, halogen, $C_1$-$C_3$ alkyl, $C_1$-$C_3$ alkoxy, $C_1$-$C_3$ alkylthio, cyclopropyl, $C_1$-$C_3$ alkylamino, or phenyl; and $R^8$ is hydrogen, $C_1$-$C_3$ alkyl, phenyl, or $C_1$-$C_3$ alkylcarbonyl;

or an agriculturally acceptable N-oxide or salt thereof.

In some of these embodiments, $R^1$ is $OR^1$. In some of these embodiments, X is CF. In some of these embodiments, A is A15. In some of these embodiments, $R^5$ is F.

In some embodiments:

X is CY, wherein Y is $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$ ($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is $C_5$-$C_8$ alkyl or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$ ($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is F, Br, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$ ($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, or A20;

$R^5$ is $C_1$-$C_4$ alkyl, $C_1$-$C_4$ haloalkyl, halocyclopropyl, $C_2$-$C_4$ alkenyl, $C_2$-$C_4$ haloalkenyl, $C_2$-$C_4$ alkynyl, $C_1$-$C_3$ haloalkoxy, $C_1$-$C_3$ alkylthio, $C_1$-$C_3$ haloalkylthio, $C_1$-$C_4$ alkylamino, or $C_2$-$C_4$ haloalkylamino;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, or A20;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently $C_1$-$C_4$ alkyl, $C_1$-$C_4$ haloalkyl, halocyclopropyl, $C_3$-$C_4$ alkenyl, $C_2$-$C_4$ haloalkenyl, $C_2$-$C_4$ alkynyl, $C_1$-$C_3$ haloalkoxy, $C_1$-$C_3$ alkylthio, $C_1$-$C_3$ haloalkylthio, $C_1$-$C_4$ alkylamino or $C_2$-$C_4$ haloalkylamino, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with $=C$ represent a 5- or 6-membered saturated ring;

A is A1, A2, A3, A4, A5, A6, A7, A8, A9, A10, A11, A12, A13, A14, A15, A16, A17, or A18;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently $C_1$-$C_4$ alkyl, $C_1$-$C_4$ haloalkyl, halocyclopropyl, $C_2$-$C_4$ alkenyl, $C_2$-$C_4$ haloalkenyl, $C_2$-$C_4$ alkynyl, $C_1$-$C_3$ haloalkoxy, $C_1$-$C_3$ haloalkylthio, amino, $C_1$-$C_4$ alkylamino, or $C_2$-$C_4$ haloalkylamino; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^{1'}$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with $=C$ represent a 5- or 6-membered saturated ring;

A is A3, A6, A11, A12, A15, A18, A19, or A20;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is $C_3$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, or $C_1$-$C_6$ trialkylsilyl.

In some of these embodiments, $R^1$ is $OR^1$. In some of these embodiments, X is CF. In some of these embodiments, A is A15. In some of these embodiments, $R^5$ is F.

In certain embodiments, the pyridine carboxylic acid herbicide can comprise a compound defined by Formula (II):

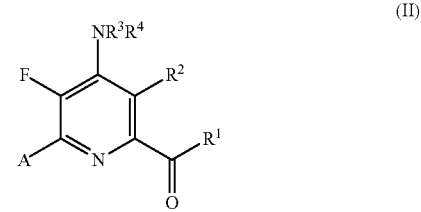

wherein $R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with $=C$ represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments:

$R^1$ is $OR^{1'}$, wherein $R^{1'}$ is hydrogen, $C_1$-$C_8$ alkyl, or $C_7$-$C_{10}$ arylalkyl;

$R^2$ is halogen, $C_1$-$C_4$ alkyl, $C_1$-$C_4$ haloalkyl, $C_2$-$C_4$-alkenyl, $C_2$-$C_4$ haloalkenyl, $C_2$-$C_4$ alkynyl, $C_1$-$C_4$-alkoxy, $C_1$-$C_4$ haloalkoxy, $C_1$-$C_4$ alkylthio, or $C_1$-$C_4$ haloalkylthio;

$R^3$ and $R^4$ are hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino;

A is A1, A2, A3, A7, A8, A9, A10, A11, A12, A13, A14, A15, A21, A22, A23, A24, A27, A28, A29, A30, A31, or A32;

$R^5$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, or $C_2$-$C_4$ haloalkylamino;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, CN, or $NO_2$;

$R^7$ and $R^{7'}$ are independently hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, cyclopropyl, amino or $C_1$-$C_4$ alkylamino; and $R^8$ is hydrogen, $C_1$-$C_6$ alkyl, $C_1$-$C_4$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, $C_1$-$C_6$ alkoxycarbonyl, or $C_1$-$C_6$ alkylcarbamyl.

In some embodiments, $R^1$ is $OR^{1'}$, wherein $R^{1'}$ is hydrogen, $C_1$-$C_8$ alkyl, or $C_7$-$C_{10}$ arylalkyl.

In some embodiments, $R^2$ is halogen, $C_2$-$C_4$-alkenyl, $C_2$-$C_4$ haloalkenyl, or $C_1$-$C_4$-alkoxy. In certain embodiments, $R^2$ is Cl, methoxy, vinyl, or 1-propenyl. In some embodiments, $R^3$ and $R^4$ are hydrogen.

In some embodiments, A is A1, A2, A3, A7, A8, A9, A10, A13, A14, or A15. In certain embodiments, A is A1, A2, A3, A13, A14, or A15. In certain embodiments, A is A15.

In some embodiments, $R^5$ is hydrogen or F. In certain embodiments, $R^5$ is F. In certain embodiments, $R^5$ is H.

In some embodiments, $R^6$ is hydrogen or F. In certain embodiments, $R^6$ is F. In certain embodiments, $R^6$ is H. In some embodiments, $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$. In certain embodiments, $R^6$, $R^{6'}$, and $R^{6''}$ are all hydrogen.

In certain embodiments, $R^2$ is Cl, methoxy, vinyl, or 1-propenyl; $R^3$ and $R^4$ are hydrogen; A is A15; $R^5$ is hydrogen or F; $R^6$ is hydrogen or F; and $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can comprise a compound defined by Formula (III):

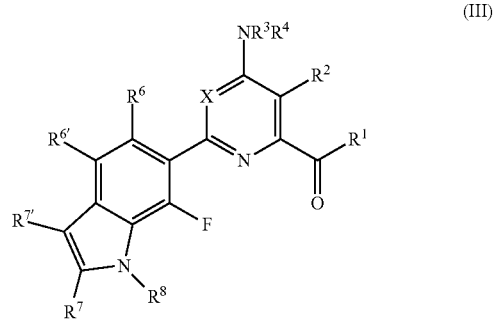

(III)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1''}$ or $NR^{1''}R^{1'''}$, wherein $R^{1''}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with $=C$ represent a 5- or 6-membered saturated ring;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;
or an agriculturally acceptable N-oxide or salt thereof.

In some embodiments:

X is N, CH, CF, CCl, or CBr;

$R^1$ is $OR^{1'}$, wherein $R^{1'}$ is hydrogen, $C_1$-$C_8$ alkyl, or $C_2$-$C_{10}$ arylalkyl;

$R^2$ is halogen, $C_1$-$C_4$ alkyl, $C_1$-$C_4$ haloalkyl, $C_2$-$C_4$-alkenyl, $C_2$-$C_4$ haloalkenyl, $C_2$-$C_4$ alkynyl, $C_1$-$C_4$-alkoxy, $C_1$-$C_4$ haloalkoxy, $C_1$-$C_4$ alkylthio, or $C_1$-$C_4$ haloalkylthio;

$R^3$ and $R^4$ are hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, CN, or $NO_2$;

$R^7$ and $R^{7'}$ are independently hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, cyclopropyl, amino or $C_1$-$C_4$ alkylamino; and $R^8$ is hydrogen, $C_1$-$C_6$ alkyl, $C_1$-$C_4$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, $C_1$-$C_6$ alkoxycarbonyl, or $C_1$-$C_6$ alkylcarbamyl.

In some embodiments, X is N, CH or CF. In some embodiments, X is N. In some embodiments, X is CH. In some embodiments, X is CF. In other embodiments, X is C—$CH_3$.

In some embodiments, $R^2$ is halogen, $C_2$-$C_4$-alkenyl, $C_2$-$C_4$ haloalkenyl, or $C_1$-$C_4$-alkoxy. In certain embodiments, $R^2$ is Cl, methoxy, vinyl, or 1-propenyl. In some embodiments, $R^3$ and $R^4$ are hydrogen.

In some embodiments, $R^6$ is hydrogen or F. In certain embodiments, $R^6$ is F. In certain embodiments, $R^6$ is H. In some embodiments, $R^{6'}$ is hydrogen, halogen, $C_1$-$C_4$ alkyl, $C_1$-$C_4$ haloalkyl, cyclopropyl, $C_2$-$C_4$ alkynyl, CN, or $NO_2$. In certain embodiments, $R^6$ and $R^{6'}$ are both hydrogen.

In certain embodiments, $R^7$ and $R^{7'}$ are both hydrogen.

In certain embodiments, $R^6$, $R^{6'}$, $R^7$, and $R^{7'}$ are all hydrogen.

In certain embodiments, X is CF, $R^1$ is $OR^{1'}$, wherein $R^{1'}$ is hydrogen, $C_1$-$C_8$ alkyl, or $C_7$-$C_{10}$ arylalkyl; $R^2$ is Cl, methoxy, vinyl, or 1-propenyl; $R^3$ and $R^4$ are hydrogen; $R^6$ is hydrogen or F; and $R^{6'}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can comprise one of Compounds 1-24, the structures of which are shown in the table below.

| Compound No. | Structure |
|---|---|
| 1 | 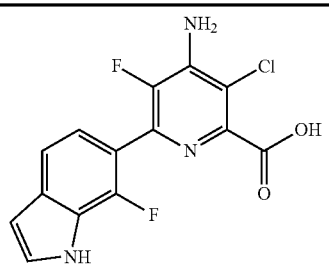 |
| 2 | 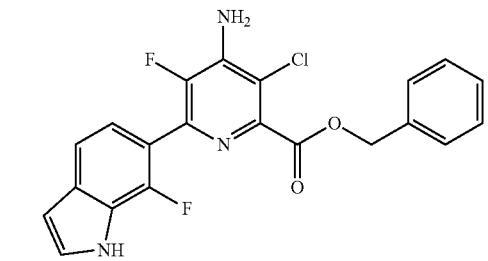 [SMILES: Nc1c(F)c(-c2ccc3cc[nH]c3c2F)nc(C(=O)OCc2ccccc2)c1Cl] |
| 3 | 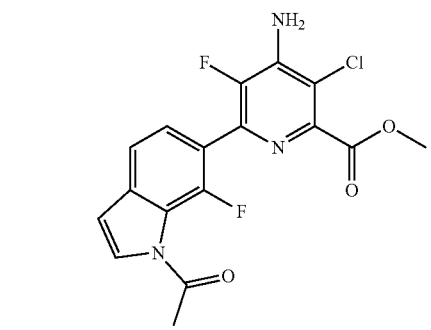 [SMILES: COC(=O)c1nc(-c2ccc3ccn(C(C)=O)c3c2F)c(F)c(N)c1Cl] |
| 4 | 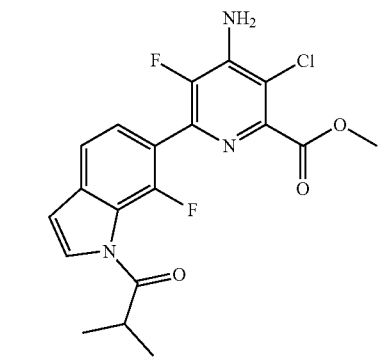 [SMILES: COC(=O)c1nc(-c2ccc3ccn(C(=O)C(C)C)c3c2F)c(F)c(N)c1Cl] |
| 5 | 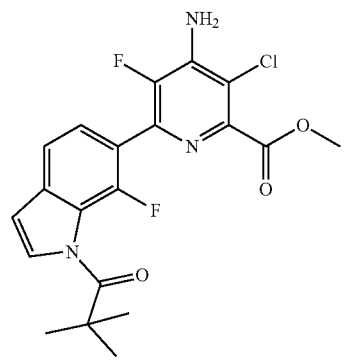 [SMILES: COC(=O)c1nc(-c2ccc3ccn(C(=O)C(C)(C)C)c3c2F)c(F)c(N)c1Cl] |

-continued
| Compound No. | Structure |
|---|---|
| 6 | 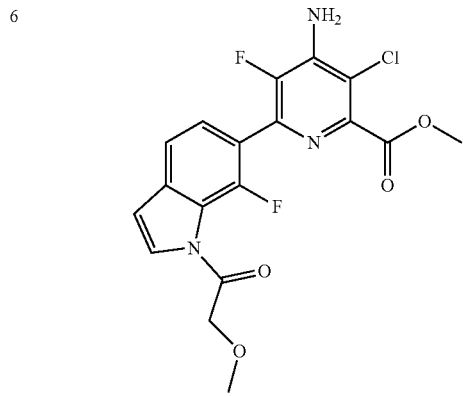 |
| 7 | 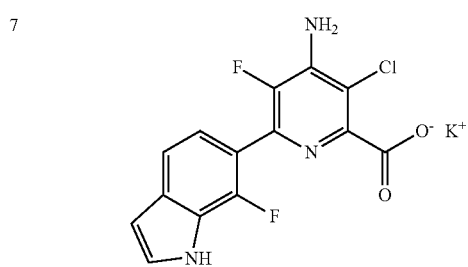 |
| 8 | 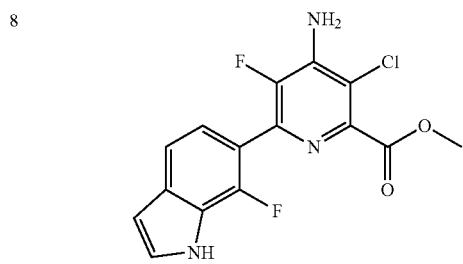 |
| 9 | 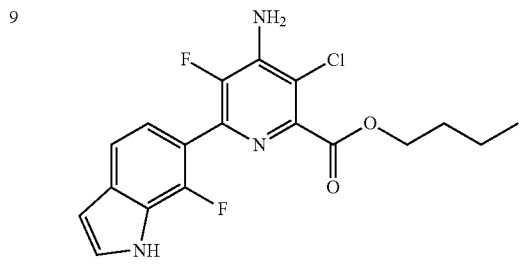 |
| 10 | 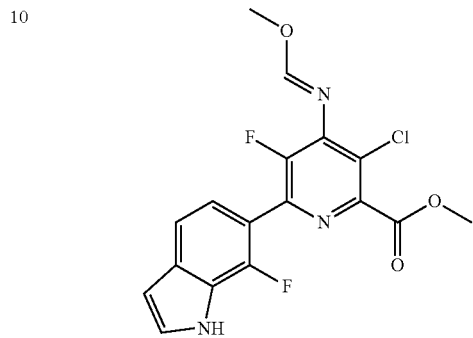 |
-continued
| Compound No. | Structure |
|---|---|
| 11 | 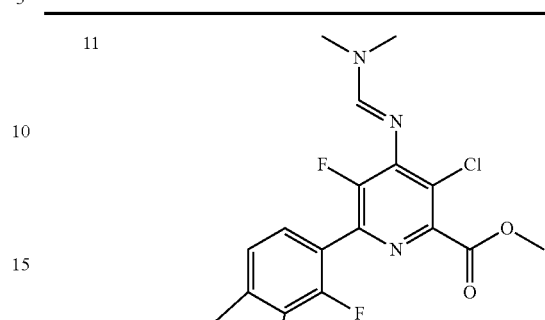 |
| 12 | 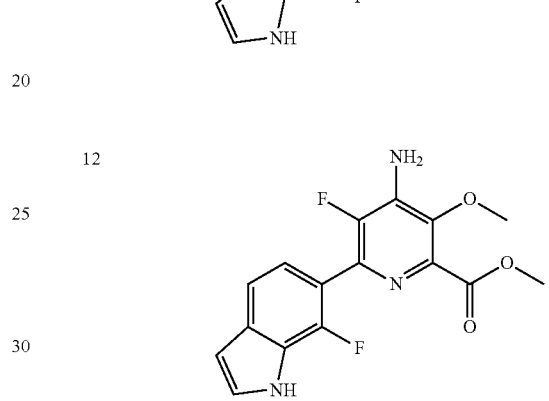 |
| 13 | 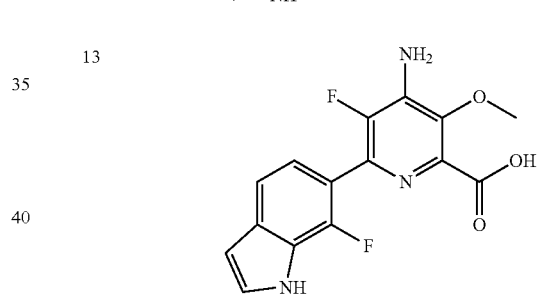 |
| 14 | 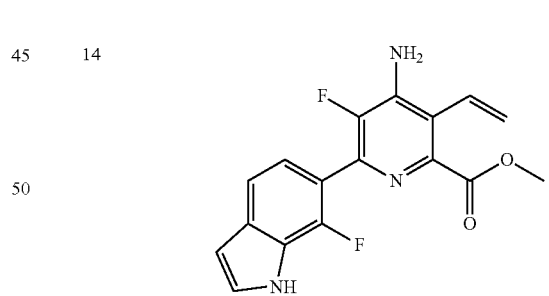 |
| 15 | 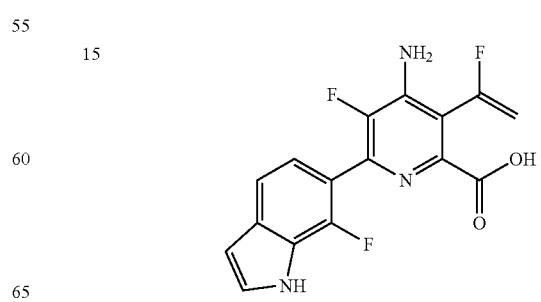 |

| Compound No. | Structure |
|---|---|
| 16 | 4-amino-3-chloro-6-(7-fluoro-1H-indol-6-yl)picolinic acid |
| 17 | 4-amino-3-chloro-5-fluoro-6-(7-fluoro-1H-indol-5-yl)picolinic acid |
| 18 | 4-amino-3-chloro-5-fluoro-6-(1H-indol-6-yl)picolinic acid |
| 19 | 4-amino-3-chloro-5-fluoro-6-(benzo[d]thiazol-6-yl)picolinic acid |
| 20 | methyl 4-amino-3-chloro-5-fluoro-6-(benzo[b]thiophen-6-yl)picolinate |
| 21 | 6-amino-2-(benzo[b]thiophen-6-yl)-5-methoxypyrimidine-4-carboxylic acid |
| 22 | 4-amino-3-chloro-5-fluoro-6-(benzofuran-6-yl)picolinic acid |
| 23 | methyl 4-amino-3-chloro-5-fluoro-6-(benzo[d]thiazol-6-yl)picolinate |
| 24 | methyl 6-amino-2-(7-fluorobenzofuran-6-yl)-5-methoxypyrimidine-4-carboxylate |

In certain embodiments, the pyridine carboxylic acid herbicide can comprise 4-amino-3-chloro-5-fluoro-6-(7-fluoro-1H-indol-6-yl) picolinic acid, or an agriculturally acceptable N-oxide, salt, or ester thereof.

In some embodiments, the pyridine carboxylic acid herbicide can be provided as an agriculturally acceptable salt. Exemplary agriculturally acceptable salts of the pyridine carboxylic acid herbicides of Formula (I) include, but are not limited to, sodium salts, potassium salts, ammonium salts or substituted ammonium salts, in particular mono-, di- and tri-$C_1$-$C_8$ alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, diglycolamine salts, choline salts, and quaternary ammonium salts such as those represented by the formula $R^9R^{10}R^{11}R^{12}N^+$ and wherein $R^9$, $R^{10}$, $R^{11}$ and $R^{12}$ (e.g., $R^9$-$R^{12}$) each independently can represent hydrogen, $C_1$-$C_{10}$ alkyl, $C_2$-$C_8$ alkenyl, $C_2$-$C_8$ alkynyl, $C_1$-$C_8$ alkoxy, $C_1$-$C_8$ alkylthio, or aryl groups, provided that $R^9$-$R^{12}$ are sterically compatible.

In some embodiments, the pyridine carboxylic acid herbicide can be provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl, butoxyethyl esters, substituted or unsubstituted aryl esters, orthoesters, substituted or unsubstituted alkylaryl esters, and substituted or unsubstituted arylalkyl esters. In some embodiments, the ester can comprise a $C_1$-$C_8$ alkyl ester, wherein the $C_1$-$C_8$ alkyl group is optionally substituted with one or more moieties selected from the group consisting of cyano, $C_2$-$C_8$ alkoxy, and $C_2$-$C_8$ alkylsulfonyl. For example, the ester can comprise a methyl, —$CH_2CN$, —$CH_2OCH_3$, —$CH_2OCH_2CH_2OCH_3$, or —$CH_2CH_2SO_2CH_3$ ester.

The ester can also be an acetal (e.g., a cyclic acetal) formed by protection of the carbonyl group in the pyridine carboxylic acid herbicides described above (e.g., by Formula (I)). For example, the pyridine carboxylic acid herbicides described above can be reacted with a suitable diol (e.g., a diol such as ethane-1,2-diol or butane-2,3-diol, for example, using standard protecting group chemistry, such as taught in Greene, et al., *Protective Groups in Organic Synthesis*, John Wiley and Sons, Fourth Edition, 2007, hereby incorporated by reference) to form a cyclic acetal. In one embodiment, the ester can be a cyclic acetal defined by the structure below, where $R^2$, $R^3$, $R^4$, X, and A are as described above.

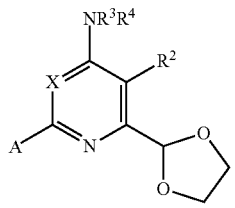

In some embodiments, the ester can comprise a substituted or unsubstituted benzyl ester. In some embodiments, the ester can comprise a benzyl ester optionally substituted with one or more moieties selected from the group consisting of halogen, $C_1$-$C_2$ alkyl, $C_1$-$C_2$ haloalkyl, and combinations thereof. In some embodiments, the ester can comprise a methyl ester.

The pyridine carboxylic acid herbicide, or an agriculturally acceptable N-oxide, salt, or ester thereof, can be applied to vegetation or an area adjacent the vegetation or applied to soil or water to prevent the emergence or growth of vegetation in an amount sufficient to induce a herbicidal effect. In some embodiments, the pyridine carboxylic acid herbicide, or an agriculturally acceptable N-oxide, salt, or ester thereof, is applied to vegetation or an area adjacent the vegetation or applied to soil or water to prevent the emergence or growth of vegetation in an amount of 0.1 grams or greater of acid equivalent per hectare (g ae/ha) (e.g., 0.2 g ae/ha or greater, 0.3 g ae/ha or greater, 0.4 g ae/ha or greater, 0.5 g ae/ha or greater, 0.6 g ae/ha or greater, 0.7 g ae/ha or greater, 0.8 g ae/ha or greater, 0.9 g ae/ha or greater, 1 g ae/ha or greater, 1.1 g ae/ha or greater, 1.2 g ae/ha or greater, 1.3 g ae/ha or greater, 1.4 g ae/ha or greater, 1.5 g ae/ha or greater, 1.6 g ae/ha or greater, 1.7 g ae/ha or greater, 1.8 g ae/ha or greater, 1.9 g ae/ha or greater, 2 g ae/ha or greater, 2.25 g ae/ha or greater, 2.5 g ae/ha or greater, 2.75 g ae/ha or greater, 3 g ae/ha or greater, 4 g ae/ha or greater, 5 g ae/ha or greater, 6 g ae/ha or greater, 7 g ae/ha or greater, 8 g ae/ha or greater, 9 g ae/ha or greater, 10 g ae/ha or greater, 11 g ae/ha or greater, 12 g ae/ha or greater, 13 g ae/ha or greater, 14 g ae/ha or greater, 15 g ae/ha or greater, 16 g ae/ha or greater, 17 g ae/ha or greater, 18 g ae/ha or greater, 19 g ae/ha or greater, 20 g ae/ha or greater, 21 g ae/ha or greater, 22 g ae/ha or greater, 23 g ae/ha or greater, 24 g ae/ha or greater, 25 g ae/ha or greater, 26 g ae/ha or greater, 27 g ae/ha or greater, 28 g ae/ha or greater, 29 g ae/ha or greater, 30 g ae/ha or greater, 31 g ae/ha or greater, 32 g ae/ha or greater, 33 g ae/ha or greater, 34 g ae/ha or greater, 35 g ae/ha or greater, 36 g ae/ha or greater, 37 g ae/ha or greater, 38 g ae/ha or greater, 39 g ae/ha or greater, 40 g ae/ha or greater, 41 g ae/ha or greater, 42 g ae/ha or greater, 43 g ae/ha or greater, 44 g ae/ha or greater, 45 g ae/ha or greater, 46 g ae/ha or greater, 47 g ae/ha or greater, 48 g ae/ha or greater, 49 g ae/ha or greater, 50 g ae/ha or greater, 55 g ae/ha or greater, 60 g ae/ha or greater, 65 g ae/ha or greater, 70 g ae/ha or greater, 75 g ae/ha or greater, 80 g ae/ha or greater, 85 g ae/ha or greater, 90 g ae/ha or greater, 95 g ae/ha or greater, 100 g ae/ha or greater, 110 g ae/ha or greater, 120 g ae/ha or greater, 130 g ae/ha or greater, 140 g ae/ha or greater, 150 g ae/ha or greater, 160 g ae/ha or greater, 170 g ae/ha or greater, 180 g ae/ha or greater, 190 g ae/ha or greater, 200 g ae/ha or greater, 210 g ae/ha or greater, 220 g ae/ha or greater, 230 g ae/ha or greater, 240 g ae/ha or greater, 250 g ae/ha or greater, 260 g ae/ha or greater, 270 g ae/ha or greater, 280 g ae/ha or greater, or 290 g ae/ha or greater).

In some embodiments, the pyridine carboxylic acid herbicide, or an agriculturally acceptable N-oxide, salt, or ester thereof, is applied to vegetation or an area adjacent the vegetation or applied to soil or water to prevent the emergence or growth of vegetation in an amount of 300 g ae/ha or less (e.g., 290 g ae/ha or less, 280 g ae/ha or less, 270 g ae/ha or less, 260 g ae/ha or less, 250 g ae/ha or less, 240 g ae/ha or less, 230 g ae/ha or less, 220 g ae/ha or less, 210 g ae/ha or less, 200 g ae/ha or less, 190 g ae/ha or less, 180 g ae/ha or less, 170 g ae/ha or less, 160 g ae/ha or less, 150 g ae/ha or less, 140 g ae/ha or less, 130 g ae/ha or less, 120 g ae/ha or less, 110 g ae/ha or less, 100 g ae/ha or less, 95 g ae/ha or less, 90 g ae/ha or less, 85 g ae/ha or less, 80 g ae/ha or less, 75 g ae/ha or less, 70 g ae/ha or less, 65 g ae/ha or less, 60 g ae/ha or less, 55 g ae/ha or less, 50 g ae/ha or less, 49 g ae/ha or less, 48 g ae/ha or less, 47 g ae/ha or less, 46 g ae/ha or less, 45 g ae/ha or less, 44 g ae/ha or less, 43 g ae/ha or less, 42 g ae/ha or less, 41 g ae/ha or less, 40 g ae/ha or less, 39 g ae/ha or less, 38 g ae/ha or less, 37 g ae/ha or less, 36 g ae/ha or less, 35 g ae/ha or less, 34 g ae/ha or less, 33 g ae/ha or less, 32 g ae/ha or less, 31 g ae/ha or less, 30 g ae/ha or less, 29 g ae/ha or less, 28 g ae/ha or less, 27 g ae/ha or less, 26 g ae/ha or less, 25 g ae/ha or less, 24 g ae/ha or less, 23 g ae/ha or less, 22 g ae/ha or less, 21 g ae/ha or less, 20 g ae/ha or less, 19 g ae/ha or less, 18 g ae/ha or less, 17 g ae/ha or less, 16 g ae/ha or less, 15 g ae/ha or less, 14 g ae/ha or less, 13 g ae/ha or less, 12 g ae/ha or less, 11 g ae/ha or less, 10 g ae/ha or less, 9 g ae/ha or less, 8 g ae/ha or less, 7 g ae/ha or less, 6 g ae/ha or less, 5 g ae/ha or less, 4 g ae/ha or less, 3 g ae/ha or less, 2.75 g ae/ha or less, 2.5 g ae/ha or less, 2.25 g ae/ha or less, 2 g ae/ha or less, 1.9 g ae/ha or less, 1.8 g ae/ha or less, 1.7 g ae/ha or less, 1.6 g ae/ha or less, 1.5 g ae/ha or less, 1.4 g ae/ha or less, 1.3 g ae/ha or less, 1.2 g ae/ha or less, 1.1 g ae/ha or less, 1 g ae/ha or less, 0.9 g ae/ha or less, 0.8 g ae/ha or less, 0.7 g ae/ha or less, 0.6 g ae/ha or less, 0.5 g ae/ha or less, 0.4 g ae/ha or less, 0.3 g ae/ha or less, or 0.2 g ae/ha or less).

The pyridine carboxylic acid herbicide, or an agriculturally acceptable N-oxide, salt, or ester thereof, can be applied to vegetation or an area adjacent the vegetation or applied to soil or water to prevent the emergence or growth of vegetation in an amount ranging from any of the minimum values described above to any of the maximum values described above. In some embodiments, the pyridine carboxylic acid herbicide, or an agriculturally acceptable N-oxide, salt, or ester thereof, is applied to vegetation or an area adjacent the vegetation or applied to soil or water to prevent the emergence or growth of vegetation in an amount of from 0.1-300 g ae/ha (e.g., from 0.1-5 g ae/ha, from 2.5-40 g ae/ha, from 0.1-40 g ae/ha, from 0.1-2.5 g ae/ha, from 2-150 g ae/ha, from 5-75 g ae/ha, from 5-40 g ae/ha, from 30-40 g ae/ha, or from 5-15 g ae/ha). In some embodiments, the pyridine carboxylic acid herbicide, or an agriculturally acceptable N-oxide, salt, or ester thereof, is applied in an amount from 30-40 g ae/ha.

Azole Carboxylate Safeners

In addition to the pyridine carboxylic acid herbicide, the compositions can further include an azole carboxylate safener, or an agriculturally acceptable salt or ester thereof. Herbicide safeners are molecules used in combination with herbicides to make them "safer"—that is, to reduce the effect of the herbicide on crop plants and to improve selectivity between crop plants and weed species being targeted by the herbicide. Herbicide safeners can be used to pre-treat crop seeds prior to planting or they can be sprayed on plants as a mixture with the herbicide.

Azoles are a class of five-membered nitrogen heterocyclic ring compounds containing at least one additional heteroatom (e.g., nitrogen, sulfur, or oxygen) within the heterocyclic ring. Examples of azoles include, for example, pyrazoles, imidazoles, thiazoles, oxazoles, isoxazoles and triazoles.

Azole carboxylate safeners are a class of safeners based on carboxylate-substituted azole moieties. Examples of azole carboxylate safeners include pyrazole carboxylate safeners, imidazole carboxylate safeners, thiazole carboxylate safeners, oxazole carboxylate safeners, isoxazole carboxylate safeners, and triazole carboxylate safeners. In some embodiments, the composition can include an azole carboxylate safener selected from the group consisting of fenchlorazole, isoxadifen, mefenpyr and agriculturally acceptable salts and esters thereof, or a combination thereof. In some embodiments, the azole carboxylate safener can include fenchlorazole-ethyl, isoxadifen-ethyl, mefenpyr-diethyl, or combinations thereof.

In some embodiments, the azole carboxylate safener can comprise fenchlorazole, shown below, or an agriculturally acceptable salt or ester thereof.

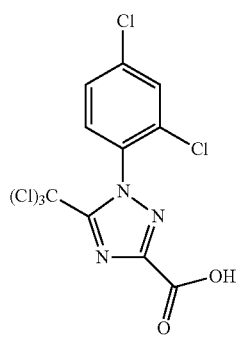

In some embodiments, the fenchlorazole is provided as an agriculturally acceptable salt or ester. An exemplary agriculturally acceptable ester of fenchlorazole is fenchlorazole ethyl, shown below.

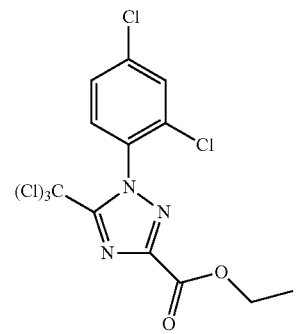

In some embodiments, the azole carboxylate safener can comprise isoxadifen, shown below, or an agriculturally acceptable salt or ester thereof.

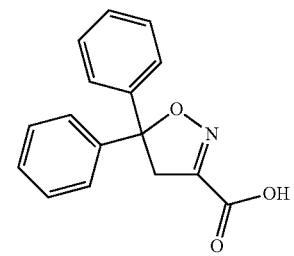 [SMILES: O=C(O)C1=NOC(c2ccccc2)(c2ccccc2)C1]

In some embodiments, the isoxadifen is provided as an agriculturally acceptable salt or ester. An exemplary agriculturally acceptable ester of isoxadifen is isoxadifen-ethyl, shown below.

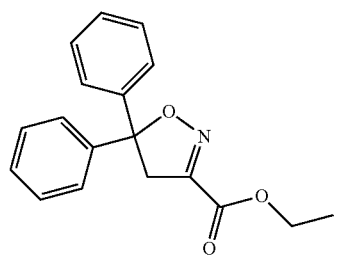 [SMILES: CCOC(=O)C1=NOC(c2ccccc2)(c2ccccc2)C1]

In some embodiments, the azole carboxylate safener can comprise mefenpyr, shown below, or an agriculturally acceptable salt or ester thereof.

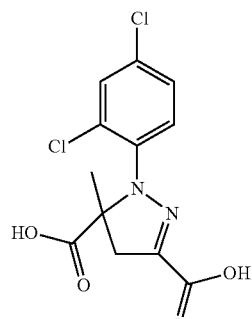

In some embodiments, the mefenpyr is provided as an agriculturally acceptable salt or ester. An exemplary agriculturally acceptable ester of mefenpyr is mefenpyr-diethyl, shown below.

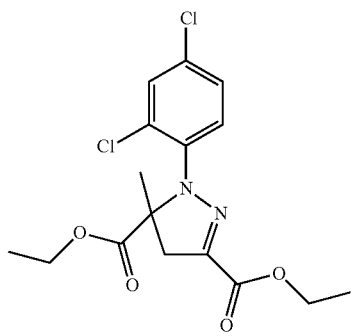 [SMILES: CCOC(=O)C1=NN(c2ccc(Cl)cc2Cl)C(C)(C(=O)OCC)C1]

The azole carboxylate safener or an agriculturally acceptable salt or ester thereof can be used in an amount sufficient to induce a safening effect. In some embodiments the azole carboxylate safener or an agriculturally acceptable salt or ester thereof is applied to vegetation or an area adjacent the vegetation or applied to soil or water in an amount of 1 grams or greater of acid equivalent per hectare (g ai/ha) (e.g., 2 g ai/ha or greater, 3 g ai/ha or greater, 4 g ai/ha or greater, 5 g ai/ha or greater, 6 g ai/ha or greater, 7 g ai/ha or greater, 8 g ai/ha or greater, 9 g ai/ha or greater, 10 g ai/ha or greater, 11 g ai/ha or greater, 12 g ai/ha or greater, 13 g ai/ha or greater, 14 g ai/ha or greater, 15 g ai/ha or greater, 16 g ai/ha or greater, 17 g ai/ha or greater, 18 g ai/ha or greater, 19 g ai/ha or greater, 20 g ai/ha or greater, 21 g ai/ha or greater, 22 g ai/ha or greater, 23 g ai/ha or greater, 24 g ai/ha or greater, 25 g ai/ha or greater, 26 g ai/ha or greater, 27 g ai/ha or greater, 28 g ai/ha or greater, 29 g ai/ha or greater, 30 g ai/ha or greater, 31 g ai/ha or greater, 32 g ai/ha or greater, 33 g ai/ha or greater, 34 g ai/ha or greater, 35 g ai/ha or greater, 36 g ai/ha or greater, 37 g ai/ha or greater, 38 g ai/ha or greater, 39 g ai/ha or greater, 40 g ai/ha or greater, 41 g ai/ha or greater, 42 g ai/ha or greater, 43 g ai/ha or greater, 44 g ai/ha or greater, 45 g ai/ha or greater, 46 g ai/ha or greater, 47 g ai/ha or greater, 48 g ai/ha or greater, 49 g ai/ha or greater, 50 g ai/ha or greater, 55 g ai/ha or greater, 60 g ai/ha or greater, 65 g ai/ha or greater, 70 g ai/ha or greater, 75 g ai/ha or greater, 80 g ai/ha or greater, 85 g ai/ha or greater, 90 g ai/ha or greater, 95 g ai/ha or greater, 100 g ai/ha or greater, 110 g ai/ha or greater, 120 g ai/ha or greater, 130 g ai/ha or greater, 140 g ai/ha or greater, 150 g ai/ha or greater, 160 g ai/ha or greater, 170 g ai/ha or greater, 180 g ai/ha or greater, 190 g ai/ha or greater, 200 g ai/ha or greater, 210 g ai/ha or greater, 220 g ai/ha or greater, 230 g ai/ha or greater, 240 g ai/ha or greater, 250 g ai/ha or greater, 260 g ai/ha or greater, 270 g ai/ha or greater, 280 g ai/ha or greater, or 290 g ai/ha or greater).

In some embodiments the azole carboxylate safener or an agriculturally acceptable salt or ester thereof is applied to vegetation or an area adjacent the vegetation or applied to soil or water in an amount of 300 g ai/ha or less (e.g., 290 g ai/ha or less, 280 g ai/ha or less, 270 g ai/ha or less, 260 g ai/ha or less, 250 g ai/ha or less, 240 g ai/ha or less, 230 g ai/ha or less, 220 g ai/ha or less, 210 g ai/ha or less, 200 g ai/ha or less, 190 g ai/ha or less, 180 g ai/ha or less, 170 g ai/ha or less, 160 g ai/ha or less, 150 g ai/ha or less, 140 g ai/ha or less, 130 g ai/ha or less, 120 g ai/ha or less, 110 g ai/ha or less, 100 g ai/ha or less, 95 g ai/ha or less, 90 g ai/ha or less, 85 g ai/ha or less, 80 g ai/ha or less, 75 g ai/ha or less, 70 g ai/ha or less, 65 g ai/ha or less, 60 g ai/ha or less, 55 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9 g ai/ha or less, 8 g ai/ha or less, 7 g ai/ha or less, 6 g ai/ha or less, 5 g ai/ha or less, 4 g ai/ha or less, 3 g ai/ha or less, or 2 g ai/ha or less).

The azole carboxylate safener or an agriculturally acceptable salt or ester thereof can be applied to vegetation or an area adjacent the vegetation or applied to soil or water in an amount ranging from any of the minimum values described above to any of the maximum values described above. In some embodiments, the azole carboxylate safener or agriculturally acceptable salt or ester thereof is applied to vegetation or an area adjacent the vegetation or applied to soil or water in an amount of from 1-300 g ai/ha (e.g., from 2-150 g ai/ha, from 5-75 g ai/ha, from 5-40 g ai/ha, from 30-40 g ai/ha, or from 5-15 g ai/ha). In some embodiments, the azole carboxylate safener or agriculturally acceptable salt or ester thereof is applied in an amount from 30-40 g ai/ha.

II. Compositions

A. Herbicidal Mixtures or Combinations

The (a) pyridine carboxylic acid herbicide, or an agriculturally acceptable N-oxide, salt, or ester thereof, can be mixed with or applied in combination with (b) an azole carboxylate safener or an agriculturally acceptable salt or ester thereof.

In some embodiments, the (a) pyridine carboxylic acid herbicide, or an agriculturally acceptable N-oxide, salt, or ester thereof, can be mixed with or applied in combination with (b) an azole carboxylate safener or an agriculturally acceptable salt or ester thereof in an amount sufficient to induce a synergistic effect. In some embodiments, (a) and (b) are used in an amount sufficient to induce a synergistic herbicidal effect while still showing good crop compatibility (i.e., their use in crops does not result in increased damage to crops or reduces damage to crops when compared to the individual application of the herbicidal compounds (a) or (b)).

As described in the *Herbicide Handbook* of the Weed Science Society of America, Tenth Edition, 2014, p. 487, "'synergism' [is] an interaction of two or more factors such that the effect when combined is greater than the predicted effect based on the response to each factor applied separately." Synergistic in the herbicide context can mean that the use of (a) and (b) as defined above results in an increased weed control effect compared to the weed control effects that are possible with the use of (a) or (b) alone. In some embodiments, the damage or injury to the undesired vegetation or the crop caused by the compositions and methods disclosed herein is evaluated using a scale from 0% to 100%, when compared with the untreated control vegetation, wherein 0% indicates no damage to the undesired vegetation and 100% indicates complete destruction of the undesired vegetation. In some embodiments, Colby's formula is applied to determine whether using (a) and (b) in combination shows a synergistic effect: S. R. Colby, *Calculating Synergistic and Antagonistic Responses of Herbicide Combinations*, WEEDS 15, p. 22 (1967)

$$E = X + Y - \frac{X*Y}{100}$$

wherein

X=effect in percent using (a) a pyridine carboxylic acid herbicide or an agriculturally acceptable N-oxide, salt, or ester thereof at an application rate a;

Y=effect in percent using (b) an azole carboxylate safener or an agriculturally acceptable salt or ester thereof at an application rate b;

E=expected effect (in %) of (a)+(b) at application rates a and b.

In Colby's equation, the value E corresponds to the effect (plant damage or injury) that is to be expected if the activity of the individual compounds is additive. If the observed effect is higher than the value E calculated according to the Colby equation, then a synergistic effect is present according to the Colby equation. Likewise, with respect to the desired crop, if the observed effect is lower than the value E calculated according to the Colby equation, then a synergistic effect is present according to the Colby equation with respect to crop safening.

In some embodiments, the compositions and methods disclosed herein are synergistic as defined by the Colby equation. In some embodiments, the joint action of (a) a pyridine carboxylic acid herbicide or an agriculturally acceptable N-oxide, salt, or ester thereof and (b) an azole carboxylate safener or an agriculturally acceptable salt or ester thereof results in enhanced activity against undesired vegetation (via synergism), even at application rates below those typically used for the pesticide to have a herbicidal effect on its own. In some embodiments, the compositions and methods disclosed herein can, based on the individual components, be used at lower application rates to achieve a herbicidal effect comparable to the effect produced by the individual components at normal application rates. In some embodiments, the compositions and methods disclosed herein provide an accelerated action on undesired vegetation (i.e. they effect damaging of undesired vegetation more quickly compared with application of the individual herbicides). In some embodiments, the joint action of (a) a pyridine carboxylic acid herbicide or an agriculturally acceptable N-oxide, salt, or ester thereof and (b) azole carboxylate safener or an agriculturally acceptable salt or ester thereof results in reduced activity against desired vegetation/crops (via synergism).

In some embodiments, the observed effect for undesired vegetation is at least 1%, at least 2%, at least 3%, at least 4%, at least 5%, at least 10%, at least 15%, at least 20%, or at least 25% greater than the effect (E) calculated according to the Colby equation (e.g., an observed effect of 96% would be 4% greater than an calculated effect (E) of 92%). In some embodiments, for undesired vegetation, the difference ($D_O$) between 100% and the observed effect is at least 5%, at least 10%, at least 15%, at least 20%, at least 25%, at least 30%, at least 35%, at least 40%, at least 45%, or at least 50% less than the difference ($D_E$) between 100% and the effect (E) calculated according to the Colby equation (e.g., an observed effect of 96% would produce a $D_O$ of 4%, a calculated effect (E) of 92% would produce a $D_E$ of 8%, and $D_O$ would be 50% less than or half of $D_E$). In some embodiments, the observed effect for desired vegetation/crops is at least 1%, at least 2%, at least 3%, at least 4%, at least 5%, at least 6%, at least 7%, at least 8%, at least 9%, or at least 10% less than the effect (E) calculated according to the Colby equation. In some embodiments, for desired vegetation/crops, the difference ($D_O$) between 100% and the observed effect is at least 2%, at least 5%, at least 10%, at least 15%, at least 20%, or at least 25% greater than the difference ($D_E$) between 100% and the effect (E) calculated according to the Colby equation.

In some embodiments, the weight ratio of (a) a pyridine carboxylic acid herbicide or an agriculturally acceptable N-oxide, salt, or ester thereof (in g ae/ha) to (b) an azole carboxylate safener, or an agriculturally acceptable salt or ester thereof (in g ai/ha) is 1:5 or more (e.g., 1:4.75 or more, 1:4.5 or more, 1:4.25 or more, 1:4 or more, 1:3.75 or more, 1:3.5 or more, 1:3.25 or more, 1:3 or more, 1:2.75 or more, 1:2.5 or more, 1:2.25 or more, 1:2 or more, 1:1.9 or more, 1:1.8 or more, 1:1.7 or more, 1:1.6 or more, 1:1.5 or more, 1:1.4 or more, 1:1.3 or more, 1:1.2 or more, 1:1.1 or more, 1:1 or more, 1.1:1 or more, 1.2:1 or more, 1.3:1 or more, 1.4:1 or more, 1.5:1 or more, 1.6:1 or more, 1.7:1 or more, 1.8:1 or more, 1.9:1 or more, 2:1 or more, 2.25:1 or more, 2.5:1 or more, 2.75:1 or more, 3:1 or more, 3.25:1 or more, 3.5:1 or more, 3.75:1 or more, 4:1 or more, 4.25:1 or more, 4.5:1 or more, 4.75:1 or more, 5:1 or more, 6:1 or more, 7:1 or more, 8:1 or more, 9:1 or more, 10:1 or more, 11:1 or more, 12:1 or more, 13:1 or more, 14:1 or more, 15:1 or more, 16:1 or more, 17:1 or more, 18:1 or more, 19:1 or more, 20:1 or more, 25:1 or more, 30:1 or more, 35:1 or more, 40:1 or more, 45:1 or more, 50:1 or more, 55:1 or more, or 60:1 or more).

In some embodiments, the weight ratio of (a) a pyridine carboxylic acid herbicide or an agriculturally acceptable N-oxide, salt, or ester thereof (in g ae/ha) to (b) an azole carboxylate safener or an agriculturally acceptable salt or ester thereof (in g ai/ha) is 65:1 or less (e.g., 60:1 or less, 55:1 or less, 50:1 or less, 45:1 or less, 40:1 or less, 35:1 or less, 30:1 or less, 25:1 or less, 20:1 or less, 19:1 or less, 18:1 or less, 17:1 or less, 16:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4.75:1 or less, 4.5:1 or less, 4.25:1 or less, 4:1 or less, 3.75:1 or less, 3.5:1 or less, 3.25:1 or less, 3:1 or less, 2.75:1 or less, 2.5:1 or less, 2.25:1 or less, 2:1 or less, 1.9:1 or less, 1.8:1 or less, 1.7:1 or less, 1.6:1 or less, 1.5:1 or less, 1.4:1 or less, 1.3:1 or less, 1.2:1 or less, 1.1:1 or less, 1:1 or less, 1:1.1 or less, 1:1.2 or less, 1:1.3 or less, 1:1.4 or less, 1:1.5 or less, 1:1.6 or less, 1:1.7 or less, 1:1.8 or less, 1:1.9 or less, 1:2 or less, 1:2.25 or less, 1:2.5 or less, 1:2.75 or less, 1:3 or less, 1:3.25 or less, 1:3.5 or less, 1:3.75 or less, 1:4 or less, 1:4.25 or less, 1:4.5 or less, or 1:4.75 or less).

The weight ratio of (a) a pyridine carboxylic acid herbicide or an agriculturally acceptable N-oxide, salt, or ester thereof (in g ae/ha) to (b) an azole carboxylate safener or an agriculturally acceptable salt or ester thereof (in g ae/ha) can range from any of the minimum ratios described above to any of the maximum values described above. In some embodiments, the weight ratio of (a) a pyridine carboxylic acid herbicide or an agriculturally acceptable N-oxide, salt, or ester thereof (in g ae/ha) to (b) an azole carboxylate safener or an agriculturally acceptable salt or ester thereof (in g ai/ha) is from 65:1 to 1:5 (e.g., from 60:1 to 1:5, from 55:1 to 1:5, from 50:1 to 1:5, from 45:1 to 1:5, from 40:1 to 1:5, from 35:1 to 1:5, from 30:1 to 1:5, from 25:1 to 1:5, from 20:1 to 1:5, from 15:1 to 1:5, from 10:1 to 1:5, from 5:1 to 1:5, 4.5:1 to 1:4.5, from 4:1 to 1:4, from 1:1 to 1:4, from 3.5:1 to 1:3.5, from 3:1 to 1:3, from 2.5:1 to 1:2.5, from 2:1 to 1:2, from 1.9:1 to 1:1.9, from 1.8:1 to 1:1.8, from 1.7:1 to 1:1.7, from 1.6:1 to 1:1.6, from 1.5:1 to 1:1.5, from 1.4:1 to 1:1.4, from 1.3:1 to 1:1.3, from 1.2:1 to 1:1.2, from 1.1:1 to 1:1.1). In some embodiments, the weight ratio of (a) a pyridine carboxylic acid herbicide or an agriculturally acceptable N-oxide, salt, or ester thereof (in g ae/ha) to (b) an azole carboxylate safener, or an agriculturally acceptable salt or ester thereof (in g ai/ha) is 1:1.

In some examples, the active ingredients in the compositions disclosed herein consist of (a) a pyridine carboxylic acid herbicide or an agriculturally acceptable N-oxide, salt, or ester thereof and (b) an azole carboxylate safener or an agriculturally acceptable salt or ester thereof.

B. Formulations

The present disclosure also relates to formulations of the compositions and methods disclosed herein. In some embodiments, the formulation can be in the form of a single package formulation including both (a) a pyridine carboxylic acid herbicide or an agriculturally acceptable N-oxide, salt, or ester thereof and (b) an azole carboxylate safener, or an agriculturally acceptable salt or ester thereof. In some embodiments, the formulation can be in the form of a single package formulation including both (a) and (b) and further including at least one additive. In some embodiments, the formulation can be in the form of a two-package formulation, wherein one package contains (a) and optionally at least one additive while the other package contains (b) and optionally at least one additive. In some embodiments of the two-package formulation, the formulation including (a) and optionally at least one additive and the formulation including (b) and optionally at least one additive are mixed before application and then applied simultaneously. In some embodiments, the mixing is performed as a tank mix (i.e., the formulations are mixed immediately before or upon dilution with water). In some embodiments, the formulation including (a) and the formulation including (b) are not mixed but are applied sequentially (in succession), for example, immediately or within 1 hour, within 2 hours, within 4 hours, within 8 hours, within 16 hours, within 24 hours, within 2 days, or within 3 days, of each other.

In some embodiments, the formulation of (a) and (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, self-emulsifying formulations, pastes, dusts, and materials for spreading or granules.

In some embodiments, (a) a pyridine carboxylic acid herbicide or an agriculturally acceptable N-oxide, salt, or ester thereof and/or (b) an azole carboxylate safener, or an agriculturally acceptable salt or ester thereof is an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

The compositions and methods disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the pyridine carboxylic acid herbicide or agriculturally acceptable N-oxide, salt, or ester thereof. In some embodiments, the additive is premixed with the azole carboxylate safener or agriculturally acceptable salt or ester thereof.

C. Other Actives

In some embodiments, the additive is an additional pesticide. For example, the compositions described herein can be applied in conjunction with one or more additional herbicides to control undesirable vegetation. The composition can be formulated with the one or more additional herbicides, tank mixed with the one or more additional herbicides, or applied sequentially with the one or more additional herbicides. Exemplary additional herbicides include, but are not limited to: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, 4-aminopicolinic acid based herbicides, such as halauxifen, halauxifen-methyl, 4-amino-3-chloro-6-(4-chloro-2-fluoro-3-methoxyphenyl)-5-fluoro-2-pyridinecarboxylic acid, benzyl 4-amino-3-chloro-6-(4-chloro-2-fluoro-3-methoxyphenyl)-5-fluoro-2-pyridinecarboxylate, and those described in U.S. Pat. Nos. 7,314,849 and 7,432,227 to Balko, et al., aminopyralid, amiprofos-methyl, amitrole, ammonium sulfamate, anilofos, anisuron, asulam, atraton, atrazine, azafenidin, aziprotryne, barban, BCPC, beflubutamid, benazolin, bencarbazone, benfluralin, benfuresate, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, borax, bromacil, bromobonil, bromobutide, bromofenoxim, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cisanilide, clacyfos, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenquinotrione, fenteracol, fenthiaprop, fentrazamide, fenuron, ferrous sulfate, flamprop, flamprop-M, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, fluroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate salts and esters, halosafen, haloxydine, hexachloroacetone, hexaflurate, hexazinone, imazamethabenz, imazapic, imazapyr, imazaquin, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazoxyfen, pyributicarb, pyriclor, pyridafol, pyridate, pyrithiobac-sodium, pyroxasulfone, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiameturon, thiazafluron, thiazopyr, thidiazimin, thidiazuron, thiencarbazone-methyl, thifensulfuron, thifensulfurn-methyl, thiobencarb, tiafenacil, tiocarbazil, tioclorim, tolpyralate, topramezone, tralkoxydim, triallate, triafamone, triasulfuron, triaziflam, tribenuron, tribenuron-methyl, tricamba, triclopyr choline salt, triclopyr esters and amines, tridiphane, trietazine, trifloxysulfuron, trifludimoxazin, trifluralin, triflusulfuron, trifop, trifopsime, trihydroxytriazine, trimeturon, tripropindan, tritac, tritosulfuron, vernolate, xylachlor and salts, esters, optically active isomers, and mixtures thereof.

In some embodiments, the additional pesticide or an agriculturally acceptable salt or ester thereof is provided in a premixed formulation with (a), (b), or combinations thereof. In some embodiments, the pyridine carboxylic acid herbicide or an agriculturally acceptable N-oxide, salt, or ester thereof is provided in a premixed formulation with an additional pesticide. In some embodiments, the azole carboxylate safener or an agriculturally acceptable salt or ester thereof is provided in a premixed formulation with an additional pesticide.

D. Adjuvants/Carriers/Colorants/Adhesives

In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, herbicide safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphate alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8 EO); tallow amine ethoxylate (15 EO); and PEG(400) dioleate-99.

In some embodiments, the additive can be an additional safener.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivatives, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like or less, esters of the above vegetable oils or less, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

In some embodiments, emulsions, pastes or oil dispersions, can be prepared by homogenizing (a) and (b) in water by means of wetting agent, tackifier, dispersant or emulsifier. In some embodiments, concentrates suitable for dilution with water are prepared, comprising (a), (b), a wetting agent, a tackifier, and a dispersant or emulsifier.

In some embodiments, powders or materials for spreading and dusts can be prepared by mixing or concomitant grinding of (a) and (b) and optionally an additional safener with a solid carrier.

In some embodiments, granules (e.g., coated granules, impregnated granules and homogeneous granules) can be prepared by binding the (a) and (b) to solid carriers.

The formulations disclosed herein can comprise a synergistic, herbicidally effective amount of (a) and (b). In some embodiments, the concentrations of (a) and (b) in the formulations can be varied. In some embodiments, the formulations comprise from 1% to 95% (e.g., from 5% to 95%, from 10% to 80%, from 20% to 70%, from 30% to 50%) by total weight of (a) and (b). In formulations designed to be employed as concentrates, (a) and (b) can be present in a concentration of from 0.1 to 98 weight percent (0.5 to 90 weight percent), based on the total weight of the formulation. Concentrates can be diluted with an inert carrier, such as water, prior to application. The diluted formulations applied to undesired vegetation or the locus of undesired vegetation can contain from 0.0006 to 8.0 weight percent of (a) and (b) (e.g., from 0.001 to 5.0 weight percent), based on the total weight of the diluted formulation.

In some embodiments, (a) and (b), independently, can be employed in a purity of from 90% to 100% (e.g., from 95% to 100%) according to nuclear magnetic resonance (NMR) spectrometry. In some embodiments, the concentrations of (a), (b), and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), and additional pesticides. In some embodiments, (a), (b), and additional pesticides, independently, can be employed in a purity of from 90% to 100% (e.g., from 95% to 100%) according to NMR spectrometry.

III. Methods of Use

The compositions disclosed herein can be applied in any known technique for applying herbicides. Exemplary application techniques include, but are not limited to, spraying, atomizing, dusting, spreading, or direct application into water (in-water). The method of application can vary depending on the intended purpose. In some embodiments, the method of application can be chosen to ensure the finest possible distribution of the compositions disclosed herein.

In some embodiments, a method of controlling undesirable vegetation which comprises contacting the vegetation or the locus thereof with or applying to the soil or water to prevent the emergence or growth of vegetation any of the compositions is disclosed herein.

The compositions disclosed herein can be applied pre-emergence (before the emergence of undesirable vegetation) or post-emergence (i.e., during and/or after emergence of the undesirable vegetation). In some embodiments, the composition is applied post-emergence to the undesirable vegetation. In some embodiments, the pyridine carboxylic acid herbicide and the azole carboxylate safener are applied simultaneously.

When the compositions are used in crops, the compositions can be applied after seeding and before or after the emergence of the crop plants. In some embodiments, the compositions disclosed herein show good crop tolerance even when the crop has already emerged and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation or applying to soil or water to prevent the emergence or growth of vegetation by spraying (e.g., foliar spraying). In some embodiments, the spraying techniques use, for example, water as carrier and spray volume rates of from 2 liters per hectare (L/ha) to 2000 L/ha (e.g., from 10-1000 L/ha or from 50-500 L/ha). In some embodiments, the compositions disclosed herein are applied by the low-volume or the ultra-low-volume method, wherein the application is in the form of micro granules. In some embodiments, wherein the compositions disclosed herein are less well tolerated by certain crop plants, the compositions can be applied with the aid of the spray apparatus in such a way that they come into little contact, if any, with the leaves of the sensitive crop plants while reaching the leaves of undesirable vegetation that grows underneath or on the bare soil (e.g., post-directed or lay-by). In some embodiments, the compositions disclosed herein can be applied as dry formulations (e.g., granules, WDGs, etc.) into water.

In some embodiments, wherein the undesirable vegetation is treated post-emergence, the compositions disclosed herein are applied by foliar application. In some embodiments, herbicidal activity is exhibited by the compounds of the mixture when they are applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action.

The compositions and methods disclosed herein can be used to control undesired vegetation in a variety of crop and non-crop applications. In some embodiments, the compositions and methods disclosed herein can be used for controlling undesired vegetation in crops. In some embodiments, the undesirable vegetation is controlled in a row crop. Exemplary crops include, but are not limited to, wheat, corn/maize, barley, triticale, rye, teff, oats, cotton, soy, sorghum, rice, sugarcane and range land (e.g., pasture grasses). In some embodiments, the compositions and methods disclosed herein can be used for controlling undesired vegetation in wheat, corn/maize, barley, tame oats, rice, or a combination thereof. In certain embodiments, the compositions and methods disclosed herein can be used for controlling undesired vegetation in wheat (*Triticum aestivum*). In certain embodiments, the compositions and methods disclosed herein can be used for controlling undesired vegetation in corn/maize (*Zea mays*, ZEAMX). In certain embodiments, the compositions and methods disclosed herein can be used for controlling undesired vegetation in barley (*Hordeum vulgare*). In certain embodiments, the compositions and methods disclosed herein can be used for controlling undesired vegetation in tame oats (*Avena* sp., AVESS). In certain embodiments, the compositions and methods disclosed herein can be used for controlling undesired vegetation in rice (*Oryza sativa*, ORYSA).

The compositions and methods disclosed herein can be used for controlling undesired vegetation in non-crop areas. Exemplary non-crop areas include, but are not limited to, turfgrass, pastures, grasslands, rangelands, fallow land, rights-of-way, aquatic settings, tree and vine, wildlife management areas, or rangeland. In some embodiments, the compositions and methods disclosed herein can be used in industrial vegetation management (IVM) or for utility, pipeline, roadside, and railroad rights-of-way applications. In some embodiments, the compositions and methods disclosed herein can also be used in forestry (e.g., for site preparation or for combating undesirable vegetation in plantation forests). In some embodiments, the compositions and methods disclosed herein can be used to control undesirable vegetation in conservation reserve program lands (CRP), trees, vines, grasslands, and grasses grown for seeds. In some embodiments, the compositions and methods disclosed herein can be used on lawns (e.g., residential, industrial, and institutional), golf courses, parks, cemeteries, athletic fields, and sod farms.

The compositions and methods disclosed herein can also be used in crop plants that are resistant to, for instance, herbicides, pathogens, and/or insects. In some embodiments, the compositions and methods disclosed herein can be used in crop plants that are resistant to one or more herbicides because of genetic engineering or breeding. In some embodiments, the compositions and methods disclosed herein can be used in crop plants that are resistant to one or more pathogens such as plant pathogenous fungi owing to genetic engineering or breeding. In some embodiments, the compositions and methods disclosed herein can be used in crop plants that are resistant to attack by insects owing to genetic engineering or breeding. Exemplary resistant crops include, but are not limited to, crops that are resistant to photosystem II inhibitors, or crop plants that, owing to introduction of the gene for *Bacillus thuringiensis* (or Bt) toxin by genetic modification, are resistant to attack by certain insects. In some embodiments, the compositions and methods described herein can be used in conjunction with glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil to control vegetation in crops tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, bromoxynil, or combinations thereof. In some embodiments, the undesirable vegetation is controlled in glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil tolerant crops possessing single, multiple or stacked traits conferring tolerance to single or multiple chemistries and/or multiple modes of action. In some embodiments, the undesirable vegetation can be controlled in a crop that is ACCase-tolerant, ALS-tolerant, or a combination thereof. The combination of (a), (b), and a complementary herbicide or salt or ester thereof can be used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix, or as sequential applications.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens), and crop improvement traits (including but not limited to yield; protein, carbohydrate, or oil content; protein, carbohydrate, or oil composition; plant stature and plant architecture).

In some embodiments, the compositions disclosed herein can be used for controlling undesirable vegetation including grasses, broadleaf weeds, sedge weeds, and combinations thereof. In some embodiments, the compositions and methods disclosed herein can be used for controlling undesirable vegetation including, but not limited to, *Polygonum* species such as wild buckwheat (*Polygonum convolvulus*), *Amaranthus* species such as pigweed (*Amaranthus retroflexus*), *Chenopodium* species such as common lambsquarters (*Chenopodium album* L.), *Sida* species such as prickly *sida* (*Sida spinosa* L.), *Ambrosia* species such as common ragweed (*Ambrosia artemisiifolia*), *Cyperus* species such as nutsedge (*Cyperus esculentus*), *Setaria* species such as giant foxtail (*Setaria faberi*), *Sorghum* species, *Acanthospermum* species, *Anthemis* species, *Atriplex* species, *Brassica* species, *Cirsium* species, *Convolvulus* species, *Conyza* species, such as horseweed (*Conyza canadensis*), *Cassia* species, *Commelina* species, *Datura* species, *Euphorbia* species, *Geranium* species, *Galinsoga* species, *Ipomoea* species such as morning-glory, *Lamium* species, *Malva* species, *Matricaria* species, *Prosopis* species, *Rumex* species, *Sisymbrium* species, *Solanum* species, *Trifolium* species, *Xanthium* species, *Veronica* species, *Viola* species such as wild pansy (*Viola tricolor*), common chickweed (*Stellaria media*), velvetleaf (*Abutilon theophrasti*), hemp sesbania (*Sesbania exaltata* Cory), *Anoda cristata, Bidens pilosa, Brassica kaber,* shepherd's purse (*Capsella bursa-pastoris*), cornflower (*Centaurea cyanus* or *Cyanus segetum*), hempnettle (*Galeopsis tetrahit*), cleavers (*Galium aparine*), *Helianthus annuus, Desmodium tortuosum, kochia* (*Kochia scoparia*), *Medicago arabica, Mercurialis annua, Myosotis arvensis,* common poppy (*Papaver rhoeas*), *Raphanus raphanistrum,* Russian thistle (*Salsola kali*), wild mustard (*Sinapis arvensis*), *Sonchus arvensis, Thlaspi arvense, Tagetes minuta, Richardia brasiliensis, Plantago major, Plantago lanceolata,* bird's-eye speedwell (*Veronica persica*) and speedwell.

In some embodiments, the undesirable vegetation includes velvetleaf (ABUTH, *Abutilon theophrasti*), pigweed (AMARE, *Amaranthus retroflexus*), winter rape (BRSNW, *Brassica napus*), lambsquarters (CHEAL, *Chenopodium album*), thistle (CIRAR, *Cirsium arvense*), nutsedge (CYPES, *Cyperus esculentus*), poinsettia (EPHHL, *Euphorbia heterophylla*), wild buckwheat (POLCO, *Polygonum convolvulus*), giant foxtail (SETFA, *Setaria faberi*), sorghum (SORVU, *Sorghum bicolor*), chickweed (STEME, *Stellaria media*), wild pansy (VIOTR, *Viola tricolor*), or a combination thereof.

The herbicidal compositions described herein can be used to control herbicide resistant or tolerant weeds. The methods employing the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidinediones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

By way of non-limiting illustration, examples of certain embodiments of the present disclosure are given below. Parts and percentages are on a per weight basis unless otherwise indicated.

EXAMPLES

Example 1

Herbicidal Activity and Effect on Crop Injury on Wheat of Fenchlorazole-Ethyl in Combination with Compounds of Formula (I) in Greenhouse Trials Methodology—Evaluation of Postemergence Herbicidal Safening in Crops: Greenhouse Trials Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters (cm²). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Stocks solutions of the safeners were prepared following the same procedure. Spray solutions of the safeners and experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters (m²) at a spray height of 18 inches (43 centimeters (cm)) above average plant canopy. Control plants were sprayed in the same manner with the solvent blank. All herbicide application (component a) rates are in g ae/ha and all safener (component b) rates are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

The safener fenchlorazole-ethyl was combined with compound 1, compound 2, compound 3, compound 4, compound 5, and compound 6, and applied to wheat (TRZAS), and the phytotoxicity of the herbicidal compositions was measured. In addition, the efficacy of the herbicidal composition on velvetleaf (ABUTH, *Abutilon theophrasti*), pigweed (AMARE, *Amaranthus retroflexus*), winter rape (BRSNW, *Brassica napus*), lambsquarters (CHEAL, *Chenopodium album*), thistle (CIRAR, *Cirsium arvense*), nutsedge (CYPES, *Cyperus esculentus*), poinsettia (EPHHL, *Euphorbia heterophylla*), wild buckwheat (POLCO, *Polygonum convolvulus*), giant foxtail (SETFA, *Setaria faberi*), sorghum (SORVU, *Sorghum bicolor*), chickweed (STEME, *Stellaria media*), and wild pansy (VIOTR, *Viola tricolor*) was evaluated. The results are summarized in Tables 1-6.

TABLE 1

Effect (% visual injury) of compound 1 on wheat (TRZAS).

| | | Application rate (g/ha) | | |
|---|---|---|---|---|
| | | compound 1 | 35 | 0 | 35 |
| | | fenchlorazole-ethyl | 0 | 35 | 35 |
| TRZAS | Obs | 39 | 0 | 10 |
| | Exp | — | — | 39 |
| | Δ | | | −29 |
| AMARE | Obs | 100 | 0 | 100 |
| | Exp | — | — | 100 |
| | Δ | | | 0 |
| BRSNW | Obs | 99 | 0 | 100 |
| | Exp | — | — | 99 |
| | Δ | | | 1 |
| EPHHL | Obs | 100 | 0 | 100 |
| | Exp | — | — | 100 |
| | Δ | | | 0 |
| POLCO | Obs | 99 | 0 | 100 |
| | Exp | — | — | 99 |
| | Δ | | | 2 |
| ABUTH | Obs | 85 | 0 | 70 |
| | Exp | — | — | 85 |
| | Δ | | | −15 |
| CIRAR | Obs | 90 | 0 | 85 |
| | Exp | — | — | 90 |
| | Δ | | | −5 | g/ha = grams per hectare
TRZAS = *Triticum aestivum* (spring wheat)
AMARE = *Amaranthus retroflexus* (pigweed)
BRSNW = *Brassica napus* (winter rape)
EPHHL = *Euphorbia heterophylla* (poinsettia)
POLCO = *Polygonum convolvulus* (wild buckwheat)
ABUTH = *Abutilon theophrasti* (velvetleaf)
CIRAR = *Cirsium arvense* (thistle)

TABLE 2

Effect (% visual injury) of compound 2 on wheat (TRZAS).

| | | Application rate (g/ha) | | |
|---|---|---|---|---|
| | | compound 2 | 35 | 0 | 35 |
| | | fenchlorazole-ethyl | 0 | 35 | 35 |
| TRZAS | Obs | 15 | 0 | 0 |
| | Exp | — | — | 15 |
| | Δ | | | −15 |
| AMARE | Obs | 100 | 0 | 100 |
| | Exp | — | — | 100 |
| | Δ | | | 0 |
| BRSNW | Obs | 100 | 0 | 100 |
| | Exp | — | — | 100 |
| | Δ | | | 0 |
| CHEAL | Obs | 97 | 0 | 100 |
| | Exp | — | — | 97 |
| | Δ | | | 3 |
| CIRAR | Obs | 70 | 0 | 80 |
| | Exp | — | — | 70 |
| | Δ | | | 10 |
| VIOTR | Obs | 40 | 0 | 70 |
| | Exp | — | — | 40 |
| | Δ | | | 30 |
| POLCO | Obs | 100 | 0 | 100 |
| | Exp | — | — | 100 |
| | Δ | | | 0 |
| SORVU | Obs | 70 | 0 | 80 |
| | Exp | — | — | 70 |
| | Δ | | | 10 |

TABLE 2-continued

Effect (% visual injury) of compound 2 on wheat (TRZAS).

| | | Application rate (g/ha) | | |
|---|---|---|---|---|
| compound 2 | | 35 | 0 | 35 |
| fenchlorazole-ethyl | | 0 | 35 | 35 |
| STEME | Obs | 100 | 0 | 100 |
| | Exp | — | — | 100 |
| | Δ | | | 0 | g/ha = grams per hectare
TRZAS = *Triticum aestivum* (spring wheat)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
VIOTR = *Viola tricolor* (wild pansy)
POLCO = *Polygonum convolvulus* (wild buckwheat)
SORVU = *Sorghum bicolor* (sorghum)
STEME = *Stellaria media* (chickweed)

TABLE 3

Effect (% visual injury) of compound 3 on wheat (TRZAS).

| | | Application rate (g/ha) | | |
|---|---|---|---|---|
| compound 3 | | 35 | 0 | 35 |
| fenchlorazole-ethyl | | 0 | 35 | 35 |
| TRZAS | Obs | 30 | 0 | 0 |
| | Exp | — | — | 30 |
| | Δ | | | −30 |
| ABUTH | Obs | 50 | 0 | 50 |
| | Exp | — | — | 50 |
| | Δ | | | 0 |
| AMARE | Obs | 75 | 0 | 90 |
| | Exp | — | — | 75 |
| | Δ | | | 15 |
| BRSNW | Obs | 30 | 0 | 30 |
| | Exp | — | — | 30 |
| | Δ | | | 0 |
| CHEAL | Obs | 85 | 0 | 97 |
| | Exp | — | — | 85 |
| | Δ | | | 12 |
| EPHHL | Obs | 100 | 0 | 100 |
| | Exp | — | — | 100 |
| | Δ | | | 0 |
| POLCO | Obs | 97 | 0 | 100 |
| | Exp | — | — | 97 |
| | Δ | | | 3 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
EPHHL = *Euphorbia heterophylla* (poinsettia)
POLCO = *Polygonum convolvulus* (wild buckwheat)

TABLE 4

Effect (% visual injury) of compound 4 on wheat (TRZAS).

| | | Application rate (g/ha) | | |
|---|---|---|---|---|
| compound 4 | | 35 | 0 | 35 |
| fenchlorazole-ethyl | | 0 | 35 | 35 |
| TRZAS | Obs | 40 | 0 | 15 |
| | Exp | — | — | 40 |
| | Δ | | | −25 |
| AMARE | Obs | 100 | 0 | 100 |
| | Exp | — | — | 100 |
| | Δ | | | 0 |
| BRSNW | Obs | 97 | 0 | 95 |
| | Exp | — | — | 97 |
| | Δ | | | −2 |
| CHEAL | Obs | 97 | 0 | 97 |
| | Exp | — | — | 97 |
| | Δ | | | 0 |
| CIRAR | Obs | 75 | 0 | 80 |
| | Exp | — | — | 75 |
| | Δ | | | 5 |
| CYPES | Obs | 0 | 0 | 10 |
| | Exp | — | — | 0 |
| | Δ | | | 10 |
| EPHHL | Obs | 100 | 0 | 100 |
| | Exp | — | — | 100 |
| | Δ | | | 0 |
| POLCO | Obs | 100 | 0 | 100 |
| | Exp | — | — | 100 |
| | Δ | | | 0 |
| STEME | Obs | 93 | 0 | 100 |
| | Exp | — | — | 93 |
| | Δ | | | 7 | g/ha = grams per hectare
TRZAS = *Triticum aestivum* (spring wheat)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
CYPES = *Cyperus esculentus* (nutsedge)
EPHHL = *Euphorbia heterophylla* (poinsettia)
POLCO = *Polygonum convolvulus* (wild buckwheat)
STEME = *Stellaria media* (chickweed)

TABLE 5

Effect (% visual injury) of compound 5 on wheat (TRZAS).

| | | Application rate (g/ha) | | |
|---|---|---|---|---|
| compound 5 | | 35 | 0 | 35 |
| fenchlorazole-ethyl | | 0 | 35 | 35 |
| TRZAS | Obs | 45 | 0 | 35 |
| | Exp | — | — | 45 |
| | Δ | | | −10 |
| ABUTH | Obs | 80 | 0 | 80 |
| | Exp | — | — | 80 |
| | Δ | | | 0 |
| AMARE | Obs | 100 | 0 | 100 |
| | Exp | — | — | 100 |
| | Δ | | | 0 |
| BRSNW | Obs | 97 | 0 | 100 |
| | Exp | — | — | 97 |
| | Δ | | | 3 |
| CHEAL | Obs | 100 | 0 | 100 |
| | Exp | — | — | 100 |
| | Δ | | | 0 |
| CIRAR | Obs | 80 | 0 | 80 |
| | Exp | — | — | 80 |
| | Δ | | | 0 |
| STEME | Obs | 85 | 0 | 93 |
| | Exp | — | — | 85 |
| | Δ | | | 8 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
STEME = *Stellaria media* (chickweed)

TABLE 6

Effect (% visual injury) of compound 6 on wheat (TRZAS).

| | | Application rate (g/ha) | | |
|---|---|---|---|---|
| | | compound 6 | 35 | 0 | 35 |
| | | fenchlorazole-ethyl | 0 | 35 | 35 |
| TRZAS | Obs | 35 | 0 | 15 |
| | Exp | — | — | 35 |
| | Δ | | | −20 |
| ABUTH | Obs | 80 | 0 | 80 |
| | Exp | — | — | 80 |
| | Δ | | | 0 |
| AMARE | Obs | 100 | 0 | 100 |
| | Exp | — | — | 100 |
| | Δ | | | 0 |
| BRSNW | Obs | 75 | 0 | 75 |
| | Exp | — | — | 75 |
| | Δ | | | 0 |
| CHEAL | Obs | 100 | 0 | 100 |
| | Exp | — | — | 100 |
| | Δ | | | 0 |
| POLCO | Obs | 97 | 0 | 100 |
| | Exp | — | — | 97 |
| | Δ | | | 3 |
| SETFA | Obs | 10 | 0 | 80 |
| | Exp | — | — | 10 |
| | Δ | | | 70 |
| STEME | Obs | 97 | 0 | 100 |
| | Exp | — | — | 97 |
| | Δ | | | 3 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
POLCO = *Polygonum convolvulus* (wild buckwheat)
SETFA = *Setaria faberi* (giant foxtail)
STEME = *Stellaria media* (chickweed)

Example 2

Herbicidal Activity and Effect on Crop Injury on Wheat of Isoxadifen-Ethyl in Combination with Compounds of Formula (I) in Greenhouse Trials Methodology—Evaluation of Postemergence Herbicidal Safening in Crops: Greenhouse Trials Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Stocks solutions of the safeners were prepared following the same procedure. Spray solutions of the safeners and experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank. All herbicide application (component a) rates are in g ae/ha and all safener (component b) rates are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

The safener isoxadifen-ethyl was combined with compound 1, compound 2, compound 3, compound 4, compound 5, and compound 6, and applied to wheat (TRZAS), and the phytotoxicity of the herbicidal compositions was measured. In addition, the efficacy of the herbicidal composition on velvetleaf (ABUTH, *Abutilon theophrasti*), pigweed (AMARE, *Amaranthus retroflexus*), winter rape (BRSNW, *Brassica napus*), lambsquarters (CHEAL, *Chenopodium album*), thistle (CIRAR, *Cirsium arvense*), wild buckwheat (POLCO, *Polygonum convolvulus*), giant foxtail (SETFA, *Setaria faberi*), chickweed (STEME, *Stellaria media*), and wild pansy (VIOTR, *Viola tricolor*) was evaluated. The results are summarized in Tables 7-12.

TABLE 7

Effect (% visual injury) of compound 1 on wheat (TRZAS).

| | | Application rate (g/ha) | | |
|---|---|---|---|---|
| | | compound 1 | 35 | 0 | 35 |
| | | isoxadifen-ethyl | 0 | 35 | 35 |
| TRZAS | Obs | 39 | 0 | 0 |
| | Exp | — | — | 39 |
| | Δ | | | −39 |
| ABUTH | Obs | 85 | 0 | 85 |
| | Exp | — | — | 85 |
| | Δ | | | 0 |
| AMARE | Obs | 100 | 0 | 100 |
| | Exp | — | — | 100 |
| | Δ | | | 0 |
| BRSNW | Obs | 99 | 0 | 100 |
| | Exp | — | — | 99 |
| | Δ | | | 1 |
| POLCO | Obs | 99 | 0 | 100 |
| | Exp | — | — | 99 |
| | Δ | | | 2 |
| VIOTR | Obs | 64 | 0 | 70 |
| | Exp | — | — | 64 |
| | Δ | | | 6 |

TABLE 7-continued

Effect (% visual injury) of compound 1 on wheat (TRZAS).

| | | Application rate (g/ha) | | |
|---|---|---|---|---|
| compound 1 | | 35 | 0 | 35 |
| isoxadifen-ethyl | | 0 | 35 | 35 |
| CHEAL | Obs | 100 | 0 | 93 |
| | Exp | — | — | 100 |
| | Δ | | | −7 |
| CIRAR | Obs | 90 | 0 | 85 |
| | Exp | — | — | 90 |
| | Δ | | | −5 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
POLCO = *Polygonum convolvulus* (wild buckwheat)
VIOTR = *Viola tricolor* (wild pansy)
CHEAL = *Chenopodium album* (lambsquarters)
CIRAR = *Cirsium arvense* (thistle)

TABLE 8

Effect (% visual injury) of compound 2 on wheat (TRZAS).

| | | Application rate (g/ha) | | |
|---|---|---|---|---|
| compound 2 | | 35 | 0 | 35 |
| isoxadifen-ethyl | | 0 | 35 | 35 |
| TRZAS | Obs | 15 | 0 | 0 |
| | Exp | — | — | 15 |
| | Δ | | | −15 |
| AMARE | Obs | 100 | 0 | 100 |
| | Exp | — | — | 100 |
| | Δ | | | 0 |
| BRSNW | Obs | 100 | 0 | 100 |
| | Exp | — | — | 100 |
| | Δ | | | 0 |
| CHEAL | Obs | 97 | 0 | 100 |
| | Exp | — | — | 97 |
| | Δ | | | 3 |
| CIRAR | Obs | 70 | 0 | 85 |
| | Exp | — | — | 70 |
| | Δ | | | 15 |
| VIOTR | Obs | 40 | 0 | 60 |
| | Exp | — | — | 40 |
| | Δ | | | 20 |
| POLCO | Obs | 100 | 0 | 100 |
| | Exp | — | — | 100 |
| | Δ | | | 0 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
VIOTR = *Viola tricolor* (wild pansy)
POLCO = *Polygonum convolvulus* (wild buckwheat)

TABLE 9

Effect (% visual injury) of compound 3 on wheat (TRZAS).

| | | Application rate (g/ha) | | |
|---|---|---|---|---|
| compound 3 | | 35 | 0 | 35 |
| isoxadifen-ethyl | | 0 | 35 | 35 |
| TRZAS | Obs | 30 | 0 | 0 |
| | Exp | — | — | 30 |
| | Δ | | | −30 |
| ABUTH | Obs | 50 | 0 | 50 |
| | Exp | — | — | 50 |
| | Δ | | | 0 |
| AMARE | Obs | 75 | 0 | 85 |
| | Exp | — | — | 75 |
| | Δ | | | 10 |
| BRSNW | Obs | 30 | 0 | 60 |
| | Exp | — | — | 30 |
| | Δ | | | 30 |
| CHEAL | Obs | 85 | 0 | 97 |
| | Exp | — | — | 85 |
| | Δ | | | 12 |
| CIRAR | Obs | 50 | 0 | 60 |
| | Exp | — | — | 50 |
| | Δ | | | 10 |
| POLCO | Obs | 97 | 0 | 100 |
| | Exp | — | — | 97 |
| | Δ | | | 3 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
POLCO = *Polygonum convolvulus* (wild buckwheat)

TABLE 10

Effect (% visual injury) of compound 4 on wheat (TRZAS).

| | | Application rate (g/ha) | | |
|---|---|---|---|---|
| compound 4 | | 35 | 0 | 35 |
| isoxadifen-ethyl | | 0 | 35 | 35 |
| TRZAS | Obs | 40 | 0 | 10 |
| | Exp | — | — | 40 |
| | Δ | | | −30 |
| ABUTH | Obs | 80 | 0 | 80 |
| | Exp | — | — | 80 |
| | Δ | | | 0 |
| AMARE | Obs | 100 | 0 | 100 |
| | Exp | — | — | 100 |
| | Δ | | | 0 |
| BRSNW | Obs | 97 | 0 | 100 |
| | Exp | — | — | 97 |
| | Δ | | | 3 |
| CHEAL | Obs | 97 | 0 | 97 |
| | Exp | — | — | 97 |
| | Δ | | | 0 |
| CIRAR | Obs | 75 | 0 | 93 |
| | Exp | — | — | 75 |
| | Δ | | | 18 |
| VIOTR | Obs | 60 | 0 | 60 |
| | Exp | — | — | 60 |
| | Δ | | | 0 |
| STEME | Obs | 93 | 0 | 95 |
| | Exp | — | — | 93 |
| | Δ | | | 2 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
VIOTR = *Viola tricolor* (wild pansy)
STEME = *Stellaria media* (chickweed)

TABLE 11

Effect (% visual injury) of compound 5 on wheat (TRZAS).

| | | Application rate (g/ha) | | |
|---|---|---|---|---|
| | compound 5 | 35 | 0 | 35 |
| | isoxadifen-ethyl | 0 | 35 | 35 |
| TRZAS | Obs | 45 | 0 | 15 |
| | Exp | — | — | 45 |
| | Δ | | | −30 |
| ABUTH | Obs | 80 | 0 | 80 |
| | Exp | — | — | 80 |
| | Δ | | | 0 |
| AMARE | Obs | 100 | 0 | 100 |
| | Exp | — | — | 100 |
| | Δ | | | 0 |
| BRSNW | Obs | 97 | 0 | 100 |
| | Exp | — | — | 97 |
| | Δ | | | 3 |
| CHEAL | Obs | 100 | 0 | 100 |
| | Exp | — | — | 100 |
| | Δ | | | 0 |
| CIRAR | Obs | 80 | 0 | 85 |
| | Exp | — | — | 80 |
| | Δ | | | 5 |
| VIOTR | Obs | 40 | 0 | 70 |
| | Exp | — | — | 40 |
| | Δ | | | 30 |
| STEME | Obs | 85 | 0 | 100 |
| | Exp | — | — | 85 |
| | Δ | | | 15 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
VIOTR = *Viola tricolor* (wild pansy)
STEME = *Stellaria media* (chickweed)

TABLE 12

Effect (% visual injury) of compound 6 on wheat (TRZAS).

| | | Application rate (g/ha) | | |
|---|---|---|---|---|
| | compound 6 | 35 | 0 | 35 |
| | isoxadifen-ethyl | 0 | 35 | 35 |
| TRZAS | Obs | 35 | 0 | 0 |
| | Exp | — | — | 35 |
| | Δ | | | −35 |
| ABUTH | Obs | 80 | 0 | 80 |
| | Exp | — | — | 80 |
| | Δ | | | 0 |
| AMARE | Obs | 100 | 0 | 100 |
| | Exp | — | — | 100 |
| | Δ | | | 0 |
| BRSNW | Obs | 75 | 0 | 95 |
| | Exp | — | — | 75 |
| | Δ | | | 20 |
| CHEAL | Obs | 100 | 0 | 100 |
| | Exp | — | — | 100 |
| | Δ | | | 0 |
| CIRAR | Obs | 75 | 0 | 80 |
| | Exp | — | — | 75 |
| | Δ | | | 5 |
| VIOTR | Obs | 30 | 0 | 80 |
| | Exp | — | — | 30 |
| | Δ | | | 50 |
| STEME | Obs | 97 | 0 | 100 |
| | Exp | — | — | 97 |
| | Δ | | | 3 |
| POLCO | Obs | 97 | 0 | 100 |
| | Exp | — | — | 97 |
| | Δ | | | 3 |
| SETFA | Obs | 10 | 0 | 60 |
| | Exp | — | — | 10 |
| | Δ | | | 50 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
VIOTR = *Viola tricolor* (wild pansy)
STEME = *Stellaria media* (chickweed)
POLCO = *Polygonum convolvulus* (wild buckwheat)
SETFA = *Setaria faberi* (giant foxtail)

Example 3

Herbicidal Activity and Effect on Crop Injury on Wheat of Mefenpyr-Diethyl in Combination with Compounds of Formula (I) in Greenhouse Trials Methodology—Evaluation of Postemergence Herbicidal Safening in Crops: Greenhouse Trials Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Stocks solutions of the safeners were prepared following the same procedure. Spray solutions of the safeners and experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank. All herbicide application (component a) rates are in g ae/ha and all safener (component b) rates are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

The safener mefenpyr-diethyl was combined with compound 1, compound 2, compound 3, compound 4, compound 5, compound 6, and applied to wheat (TRZAS), and the phytotoxicity of the herbicidal compositions was measured. In addition, the efficacy of the herbicidal composition on velvetleaf (ABUTH, *Abutilon theophrasti*), pigweed (AMARE, *Amaranthus retroflexus*), winter rape (BRSNW, *Brassica napus*), lambsquarters (CHEAL, *Chenopodium album*), thistle (CIRAR, *Cirsium arvense*), wild buckwheat (POLCO, *Polygonum convolvulus*), sorghum (SORVU, *Sorghum bicolor*), chickweed (STEME, *Stellaria media*), and wild pansy (VIOTR, *Viola tricolor*) was evaluated. The results are summarized in Tables 13-18.

TABLE 13

Effect (% visual injury) of compound 1 on wheat (TRZAS).

| | | Application rate (g/ha) | | |
|---|---|---|---|---|
| | compound 1 | 35 | 0 | 35 |
| | mefenpyr-diethyl | 0 | 35 | 35 |
| TRZAS | Obs | 39 | 0 | 0 |
| | Exp | — | — | 39 |
| | Δ | | | −39 |
| ABUTH | Obs | 85 | 0 | 85 |
| | Exp | — | — | 85 |
| | Δ | | | 0 |
| AMARE | Obs | 100 | 0 | 100 |
| | Exp | — | — | 100 |
| | Δ | | | 0 |
| BRSNW | Obs | 99 | 0 | 100 |
| | Exp | — | — | 99 |
| | Δ | | | 1 |
| CHEAL | Obs | 100 | 0 | 100 |
| | Exp | — | — | 100 |
| | Δ | | | 0 |
| STEME | Obs | 100 | 0 | 100 |
| | Exp | — | — | 100 |
| | Δ | | | 0 |
| POLCO | Obs | 99 | 0 | 100 |
| | Exp | — | — | 99 |
| | Δ | | | 2 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
STEME = *Stellaria media* (chickweed)
POLCO = *Polygonum convolvulus* (wild buckwheat)

TABLE 14

Effect (% visual injury) of compound 2 on wheat (TRZAS).

| | | Application rate (g/ha) | | |
|---|---|---|---|---|
| | compound 2 | 35 | 0 | 35 |
| | mefenpyr-diethyl | 0 | 35 | 35 |
| TRZAS | Obs | 15 | 0 | 0 |
| | Exp | — | — | 15 |
| | Δ | | | −15 |
| AMARE | Obs | 100 | 0 | 100 |
| | Exp | — | — | 100 |
| | Δ | | | 0 |
| BRSNW | Obs | 100 | 0 | 100 |
| | Exp | — | — | 100 |
| | Δ | | | 0 |
| CHEAL | Obs | 97 | 0 | 100 |
| | Exp | — | — | 97 |
| | Δ | | | 3 |
| CIRAR | Obs | 70 | 0 | 85 |
| | Exp | — | — | 70 |
| | Δ | | | 15 |
| POLCO | Obs | 100 | 0 | 100 |
| | Exp | — | — | 100 |
| | Δ | | | 0 | g/ha = grams per hectare
TRZAS = *Triticum aestivum* (spring wheat)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
POLCO = *Polygonum convolvulus* (wild buckwheat)

TABLE 15

Effect (% visual injury) of compound 3 on wheat (TRZAS).

| | | Application rate (g/ha) | | |
|---|---|---|---|---|
| | compound 3 | 35 | 0 | 35 |
| | mefenpyr-diethyl | 0 | 35 | 35 |
| TRZAS | Obs | 30 | 0 | 10 |
| | Exp | — | — | 30 |
| | Δ | | | −20 |
| ABUTH | Obs | 50 | 0 | 50 |
| | Exp | — | — | 50 |
| | Δ | | | 0 |
| AMARE | Obs | 75 | 0 | 95 |
| | Exp | — | — | 75 |
| | Δ | | | 20 |
| BRSNW | Obs | 30 | 0 | 60 |
| | Exp | — | — | 30 |
| | Δ | | | 30 |
| CHEAL | Obs | 85 | 0 | 97 |
| | Exp | — | — | 85 |
| | Δ | | | 12 |
| CIRAR | Obs | 50 | 0 | 50 |
| | Exp | — | — | 50 |
| | Δ | | | 0 |
| POLCO | Obs | 97 | 0 | 97 |
| | Exp | — | — | 97 |
| | Δ | | | 0 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
POLCO = *Polygonum convolvulus* (wild buckwheat)

TABLE 16

Effect (% visual injury) of compound 4 on wheat (TRZAS).

| | | Application rate (g/ha) | | |
|---|---|---|---|---|
| | | compound 4 | 35 | 0 | 35 |
| | | mefenpyr-diethyl | 0 | 35 | 35 |
| TRZAS | Obs | 40 | 0 | 10 |
| | Exp | — | — | 40 |
| | Δ | | | −30 |
| ABUTH | Obs | 80 | 0 | 80 |
| | Exp | — | — | 80 |
| | Δ | | | 0 |
| AMARE | Obs | 100 | 0 | 100 |
| | Exp | — | — | 100 |
| | Δ | | | 0 |
| BRSNW | Obs | 97 | 0 | 97 |
| | Exp | — | — | 97 |
| | Δ | | | 0 |
| CHEAL | Obs | 97 | 0 | 100 |
| | Exp | — | — | 97 |
| | Δ | | | 3 |
| CIRAR | Obs | 75 | 0 | 85 |
| | Exp | — | — | 75 |
| | Δ | | | 10 |
| VIOTR | Obs | 60 | 0 | 70 |
| | Exp | — | — | 60 |
| | Δ | | | 10 |
| POLCO | Obs | 100 | 0 | 100 |
| | Exp | — | — | 100 |
| | Δ | | | 0 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
VIOTR = *Viola tricolor* (wild pansy)
POLCO = *Polygonum convolvulus* (wild buckwheat)

TABLE 17

Effect (% visual injury) of compound 5 on wheat (TRZAS).

| | | Application rate (g/ha) | | |
|---|---|---|---|---|
| | | compound 5 | 35 | 0 | 35 |
| | | mefenpyr-diethyl | 0 | 35 | 35 |
| TRZAS | Obs | 45 | 0 | 20 |
| | Exp | — | — | 45 |
| | Δ | | | −25 |
| ABUTH | Obs | 80 | 0 | 80 |
| | Exp | — | — | 80 |
| | Δ | | | 0 |
| AMARE | Obs | 100 | 0 | 100 |
| | Exp | — | — | 100 |
| | Δ | | | 0 |
| BRSNW | Obs | 97 | 0 | 100 |
| | Exp | — | — | 97 |
| | Δ | | | 3 |
| CHEAL | Obs | 100 | 0 | 100 |
| | Exp | — | — | 100 |
| | Δ | | | 0 |
| CIRAR | Obs | 80 | 0 | 85 |
| | Exp | — | — | 80 |
| | Δ | | | 5 |
| SORVU | Obs | 60 | 0 | 80 |
| | Exp | — | — | 60 |
| | Δ | | | 20 |
| STEME | Obs | 85 | 0 | 85 |
| | Exp | — | — | 85 |
| | Δ | | | 0 |
| VIOTR | Obs | 40 | 0 | 50 |
| | Exp | — | — | 40 |
| | Δ | | | 10 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
SORVU = *Sorghum bicolor* (sorghum)
STEME = *Stellaria media* (chickweed)
VIOTR = *Viola tricolor* (wild pansy)

TABLE 18

Effect (% visual injury) of compound 6 on wheat (TRZAS).

| | | Application rate (g/ha) | | |
|---|---|---|---|---|
| | | compound 6 | 35 | 0 | 35 |
| | | mefenpyr-diethyl | 0 | 35 | 35 |
| TRZAS | Obs | 35 | 0 | 10 |
| | Exp | — | — | 35 |
| | Δ | | | −25 |
| ABUTH | Obs | 80 | 0 | 80 |
| | Exp | — | — | 80 |
| | Δ | | | 0 |
| AMARE | Obs | 100 | 0 | 100 |
| | Exp | — | — | 100 |
| | Δ | | | 0 |
| BRSNW | Obs | 75 | 0 | 90 |
| | Exp | — | — | 75 |
| | Δ | | | 15 |
| CHEAL | Obs | 100 | 0 | 100 |
| | Exp | — | — | 100 |
| | Δ | | | 0 |
| VIOTR | Obs | 30 | 0 | 40 |
| | Exp | — | — | 30 |
| | Δ | | | 10 |
| POLCO | Obs | 97 | 0 | 100 |
| | Exp | — | — | 97 |
| | Δ | | | 3 | g/ha = grams per hectare
TRZAS = *Triticum aestivum* (spring wheat)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
VIOTR = *Viola tricolor* (wild pansy)
POLCO = *Polygonum convolvulus* (wild buckwheat)

Example 4

Herbicidal Activity and Effect on Crop Injury on Corn/Maize of Fenchlorazole-Ethyl in Combination with Compounds of Formula (I) in Greenhouse Trials Methodology—Evaluation of Postemergence Herbicidal Safening in Crops: Greenhouse Trials Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Stocks solutions of the safeners were prepared following the same procedure. Spray solutions of the safeners and experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank. All herbicide application (component a) rates are in g ae/ha and all safener (component b) rates are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

The safener fenchlorazole-ethyl was combined with compound 1, compound 2, compound 5, and compound 6, and applied to corn/maize (ZEAMX) and the phytotoxicity of the herbicidal compositions was measured. In addition, the efficacy of the herbicidal composition on velvetleaf (ABUTH, *Abutilon theophrasti*), pigweed (AMARE, *Amaranthus retroflexus*), winter rape (BRSNW, *Brassica napus*), lambsquarters (CHEAL, *Chenopodium album*), thistle (CIRAR, *Cirsium arvense*), nutsedge (CYPES, *Cyperus esculentus*), poinsettia (EPHHL, *Euphorbia heterophylla*), wild buckwheat (POLCO, *Polygonum convolvulus*), giant foxtail (SETFA, *Setaria faberi*), sorghum (SORVU, *Sorghum bicolor*), and chickweed (STEME, *Stellaria media*) was evaluated. The results are summarized in Tables 19-22.

TABLE 19

Effect (% visual injury) of compound 1 on corn/maize (ZEAMX).

| | | Application rate (g/ha) | | |
|---|---|---|---|---|
| | | compound 1 | 35 | 0 | 35 |
| | | fenchlorazole-ethyl | 0 | 35 | 35 |
| ZEAMX | Obs | 40 | 0 | 35 |
| | Exp | — | — | 40 |
| | Δ | | | −5 |
| AMARE | Obs | 100 | 0 | 100 |
| | Exp | — | — | 100 |
| | Δ | | | 0 |
| BRSNW | Obs | 99 | 0 | 100 |
| | Exp | — | — | 99 |
| | Δ | | | 1 |
| CHEAL | Obs | 100 | 0 | 93 |
| | Exp | — | — | 100 |
| | Δ | | | −7 |
| CIRAR | Obs | 90 | 0 | 85 |
| | Exp | — | — | 90 |
| | Δ | | | −5 |
| EPHHL | Obs | 100 | 0 | 100 |
| | Exp | — | — | 100 |
| | Δ | | | 0 |
| POLCO | Obs | 99 | 0 | 100 |
| | Exp | — | — | 99 |
| | Δ | | | 2 |
| STEME | Obs | 100 | 0 | 100 |
| | Exp | — | — | 100 |
| | Δ | | | 0 | g/ha = grams per hectare
ZEAMX = *Zea mays* (corn/maize)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
EPHHL = *Euphorbia heterophylla* (poinsettia)
POLCO = *Polygonum convolvulus* (wild buckwheat)
STEME = *Stellaria media* (chickweed)

TABLE 20

Effect (% visual injury) of compound 4 on corn/maize (ZEAMX).

| | | Application rate (g/ha) | | |
|---|---|---|---|---|
| | | compound 4 | 35 | 0 | 35 |
| | | fenchlorazole-ethyl | 0 | 35 | 35 |
| ZEAMX | Obs | 35 | 0 | 25 |
| | Exp | — | — | 35 |
| | Δ | | | −10 |
| ABUTH | Obs | 80 | 0 | 70 |
| | Exp | — | — | 80 |
| | Δ | | | −10 |
| AMARE | Obs | 100 | 0 | 100 |
| | Exp | — | — | 100 |
| | Δ | | | 0 |
| BRSNW | Obs | 97 | 0 | 95 |
| | Exp | — | — | 97 |
| | Δ | | | −2 |
| CHEAL | Obs | 97 | 0 | 97 |
| | Exp | — | — | 97 |
| | Δ | | | 0 |
| CIRAR | Obs | 75 | 0 | 80 |
| | Exp | — | — | 75 |
| | Δ | | | 5 |
| CYPES | Obs | 0 | 0 | 10 |
| | Exp | — | — | 0 |
| | Δ | | | 10 |
| EPHHL | Obs | 100 | 0 | 100 |
| | Exp | — | — | 100 |
| | Δ | | | 0 |
| POLCO | Obs | 100 | 0 | 100 |
| | Exp | — | — | 100 |
| | Δ | | | 0 |

TABLE 20-continued

Effect (% visual injury) of compound 4 on corn/maize (ZEAMX).

| | | Application rate (g/ha) | | |
|---|---|---|---|---|
| | compound 4 | 35 | 0 | 35 |
| | fenchlorazole-ethyl | 0 | 35 | 35 |
| SORVU | Obs | 80 | 0 | 80 |
| | Exp | — | — | 80 |
| | Δ | | | 0 |
| STEME | Obs | 93 | 0 | 100 |
| | Exp | — | — | 93 |
| | Δ | | | 7 | g/ha = grams per hectare
ZEAMX = *Zea mays* (corn/maize)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
CYPES = *Cyperus esculentus* (nutsedge)
EPHHL = *Euphorbia heterophylla* (poinsettia)
POLCO = *Polygonum convolvulus* (wild buckwheat)
SORVU = *Sorghum bicolor* (sorghum)
STEME = *Stellaria media* (chickweed)

TABLE 21

Effect (% visual injury) of compound 5 on corn/maize (ZEAMX).

| | | Application rate (g/ha) | | |
|---|---|---|---|---|
| | compound 5 | 35 | 0 | 35 |
| | fenchlorazole-ethyl | 0 | 35 | 35 |
| ZEAMX | Obs | 35 | 0 | 20 |
| | Exp | — | — | 35 |
| | Δ | | | -15 |
| ABUTH | Obs | 80 | 0 | 80 |
| | Exp | — | — | 80 |
| | Δ | | | 0 |
| AMARE | Obs | 100 | 0 | 100 |
| | Exp | — | — | 100 |
| | Δ | | | 0 |
| BRSNW | Obs | 97 | 0 | 100 |
| | Exp | — | — | 97 |
| | Δ | | | 3 |
| CHEAL | Obs | 100 | 0 | 100 |
| | Exp | — | — | 100 |
| | Δ | | | 0 |
| CIRAR | Obs | 80 | 0 | 80 |
| | Exp | — | — | 80 |
| | Δ | | | 0 |
| EPHHL | Obs | 100 | 0 | 100 |
| | Exp | — | — | 100 |
| | Δ | | | 0 |
| POLCO | Obs | 100 | 0 | 100 |
| | Exp | — | — | 100 |
| | Δ | | | 0 |
| SORVU | Obs | 60 | 0 | 60 |
| | Exp | — | — | 60 |
| | Δ | | | 0 |
| STEME | Obs | 85 | 0 | 93 |
| | Exp | — | — | 85 |
| | Δ | | | 8 | g/ha = grams per hectare
ZEAMX = *Zea mays* (corn/maize)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
EPHHL = *Euphorbia heterophylla* (poinsettia)
POLCO = *Polygonum convolvulus* (wild buckwheat)
SORVU = *Sorghum bicolor* (sorghum)
STEME = *Stellaria media* (chickweed)

TABLE 22

Effect (% visual injury) of compound 6 on corn/maize (ZEAMX).

| | | Application rate (g/ha) | | |
|---|---|---|---|---|
| | compound 6 | 35 | 0 | 35 |
| | fenchlorazole-ethyl | 0 | 35 | 35 |
| ZEAMX | Obs | 25 | 0 | 10 |
| | Exp | — | — | 25 |
| | Δ | | | -15 |
| ABUTH | Obs | 80 | 0 | 80 |
| | Exp | — | — | 80 |
| | Δ | | | 0 |
| AMARE | Obs | 100 | 0 | 100 |
| | Exp | — | — | 100 |
| | Δ | | | 0 |
| BRSNW | Obs | 75 | 0 | 75 |
| | Exp | — | — | 75 |
| | Δ | | | 0 |
| CHEAL | Obs | 100 | 0 | 100 |
| | Exp | — | — | 100 |
| | Δ | | | 0 |
| EPHHL | Obs | 100 | 0 | 100 |
| | Exp | — | — | 100 |
| | Δ | | | 0 |
| POLCO | Obs | 97 | 0 | 100 |
| | Exp | — | — | 97 |
| | Δ | | | 3 |
| SETFA | Obs | 10 | 0 | 80 |
| | Exp | — | — | 10 |
| | Δ | | | 70 |
| SORVU | Obs | 70 | 0 | 70 |
| | Exp | — | — | 70 |
| | Δ | | | 0 |
| STEME | Obs | 97 | 0 | 100 |
| | Exp | — | — | 97 |
| | Δ | | | 3 | g/ha = grams per hectare
ZEAMX = *Zea mays* (corn/maize)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
EPHHL = *Euphorbia heterophylla* (poinsettia)
POLCO = *Polygonum convolvulus* (wild buckwheat)
SETFA = *Setaria faberi* (giant foxtail)
SORVU = *Sorghum bicolor* (sorghum)
STEME = *Stellaria media* (chickweed)

Example 5

Herbicidal Activity and Effect on Crop Injury on Corn/Maize of Mefenpyr-Diethyl in Combination with Compounds of Formula (I) in Greenhouse Trials Methodology—Evaluation of Postemergence Herbicidal Safening in Crops: Greenhouse Trials Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters (cm²). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Stocks solutions of the safeners were prepared following the same procedure. Spray solutions of the safeners and experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank. All herbicide application (component a) rates are in g ae/ha and all safener (component b) rates are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants as compared with that of the control plants was determined visually and scored on a scale of 0 to 100 percent, where 0 corresponds to no injury and 100 corresponds to complete kill. Colby's equation was used to determine the herbicidal effects expected from the mixtures.

The safener mefenpyr-diethyl was combined with compound 1, compound 2, and compound 5, and applied to corn/maize (ZEAMX) and the phytotoxicity of the herbicidal compositions were measured. In addition, the efficacy of the herbicidal composition on velvetleaf (ABUTH, *Abutilon theophrasti*), pigweed (AMARE, *Amaranthus retroflexus*), winter rape (BRSNW, *Brassica napus*), lambsquarters (CHEAL, *Chenopodium album*), thistle (CIRAR, *Cirsium arvense*), nutsedge (CYPES, *Cyperus esculentus*), poinsettia (EPHHL, *Euphorbia heterophylla*), wild buckwheat (POLCO, *Polygonum convolvulus*), sorghum (SORVU, *Sorghum bicolor*), chickweed (STEME, *Stellaria media*), and wild pansy (VIOTR, *Viola tricolor*) was evaluated. The results are summarized in Tables 23-25.

TABLE 23

Effect (% visual injury) of compound 1 on corn/maize (ZEAMX).

| | | Application rate (g/ha) | | |
|---|---|---|---|---|
| | | compound 1 | 35 | 0 | 35 |
| | | mefenpyr-diethyl | 0 | 35 | 35 |
| ZEAMX | Obs | 40 | 0 | 30 |
| | Exp | — | — | 40 |
| | Δ | | | −10 |
| ABUTH | Obs | 85 | 0 | 85 |
| | Exp | — | — | 85 |
| | Δ | | | 0 |
| AMARE | Obs | 100 | 0 | 100 |
| | Exp | — | — | 100 |
| | Δ | | | 0 |

TABLE 23-continued

Effect (% visual injury) of compound 1 on corn/maize (ZEAMX).

| | | Application rate (g/ha) | | |
|---|---|---|---|---|
| | | compound 1 | 35 | 0 | 35 |
| | | mefenpyr-diethyl | 0 | 35 | 35 |
| BRSNW | Obs | 99 | 0 | 100 |
| | Exp | — | — | 99 |
| | Δ | | | 1 |
| CHEAL | Obs | 100 | 0 | 100 |
| | Exp | — | — | 100 |
| | Δ | | | 0 |
| EPHHL | Obs | 100 | 0 | 100 |
| | Exp | — | — | 100 |
| | Δ | | | 0 |
| POLCO | Obs | 99 | 0 | 100 |
| | Exp | — | — | 99 |
| | Δ | | | 2 |
| STEME | Obs | 100 | 0 | 100 |
| | Exp | — | — | 100 |
| | Δ | | | 0 | g/ha = grams per hectare
ZEAMX = *Zea mays* (corn/maize)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
EPHHL = *Euphorbia heterophylla* (poinsettia)
POLCO = *Polygonum convolvulus* (wild buckwheat)
STEME = *Stellaria media* (chickweed)

TABLE 24

Effect (% visual injury) of compound 2 on corn/maize (ZEAMX).

| | | Application rate (g/ha) | | |
|---|---|---|---|---|
| | | compound 2 | 35 | 0 | 35 |
| | | mefenpyr-diethyl | 0 | 35 | 35 |
| ZEAMX | Obs | 35 | 0 | 15 |
| | Exp | — | — | 35 |
| | Δ | | | −20 |
| ABUTH | Obs | 80 | 0 | 75 |
| | Exp | — | — | 80 |
| | Δ | | | −5 |
| AMARE | Obs | 100 | 0 | 100 |
| | Exp | — | — | 100 |
| | Δ | | | 0 |
| BRSNW | Obs | 100 | 0 | 100 |
| | Exp | — | — | 100 |
| | Δ | | | 0 |
| CHEAL | Obs | 97 | 0 | 100 |
| | Exp | — | — | 97 |
| | Δ | | | 3 |
| CIRAR | Obs | 70 | 0 | 85 |
| | Exp | — | — | 70 |
| | Δ | | | 15 |
| EPHHL | Obs | 100 | 0 | 100 |
| | Exp | — | — | 100 |
| | Δ | | | 0 |
| POLCO | Obs | 100 | 0 | 100 |
| | Exp | — | — | 100 |
| | Δ | | | 0 | g/ha = grams per hectare
ZEAMX = *Zea mays* (corn/maize)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
EPHHL = *Euphorbia heterophylla* (poinsettia)
POLCO = *Polygonum convolvulus* (wild buckwheat)

TABLE 25

Effect (% visual injury) of compound 5 on corn/maize (ZEAMX).

| | | Application rate (g/ha) | | |
|---|---|---|---|---|
| | | compound 5 | 35 | 0 | 35 |
| | | mefenpyr-diethyl | 0 | 35 | 35 |
| ZEAMX | Obs | | 35 | 0 | 25 |
| | Exp | | — | — | 35 |
| | Δ | | | | −10 |
| ABUTH | Obs | | 80 | 0 | 80 |
| | Exp | | — | — | 80 |
| | Δ | | | | 0 |
| AMARE | Obs | | 100 | 0 | 100 |
| | Exp | | — | — | 100 |
| | Δ | | | | 0 |
| BRSNW | Obs | | 97 | 0 | 100 |
| | Exp | | — | — | 97 |
| | Δ | | | | 3 |
| CHEAL | Obs | | 100 | 0 | 100 |
| | Exp | | — | — | 100 |
| | Δ | | | | 0 |
| CIRAR | Obs | | 80 | 0 | 85 |
| | Exp | | — | — | 80 |
| | Δ | | | | 5 |
| CYPES | Obs | | 0 | 0 | 0 |
| | Exp | | — | — | 0 |
| | Δ | | | | 0 |
| EPHHL | Obs | | 100 | 0 | 100 |
| | Exp | | — | — | 100 |
| | Δ | | | | 0 |
| POLCO | Obs | | 100 | 0 | 100 |
| | Exp | | — | — | 100 |
| | Δ | | | | 0 |
| SORVU | Obs | | 60 | 0 | 80 |
| | Exp | | — | — | 60 |
| | Δ | | | | 20 |
| VIOTR | Obs | | 40 | 0 | 50 |
| | Exp | | — | — | 40 |
| | Δ | | | | 10 | g/ha = grams per hectare
ZEAMX = *Zea mays* (corn/maize)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
CYPES = *Cyperus esculentus* (nutsedge)
EPHHL = *Euphorbia heterophylla* (poinsettia)
POLCO = *Polygonum convolvulus* (wild buckwheat)
SORVU = *Sorghum bicolor* (sorghum)
VIOTR = *Viola tricolor* (wild pansy)

Example 6

Herbicidal Activity and Effect on Crop Injury on Corn/Maize of Isoxadifen-Ethyl in Combination with Compounds of Formula (I) in Greenhouse Trials Methodology—Evaluation of Postemergence Herbicidal Safening in Crops: Greenhouse Trials Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Stocks solutions of the safeners were prepared following the same procedure. Spray solutions of the safeners and experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank. All herbicide application (component a) rates are in g ae/ha and all safener (component b) rates are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

The safener isoxadifen-ethyl was combined with compound 1, compound 2, compound 4, compound 5, and compound 6, and applied to corn/maize (ZEAMX) and the phytotoxicity of the herbicidal compositions was measured. In addition, the efficacy of the herbicidal composition on velvetleaf (ABUTH, *Abutilon theophrasti*), pigweed (AMARE, *Amaranthus retroflexus*), winter rape (BRSNW, *Brassica napus*), lambsquarters (CHEAL, *Chenopodium album*), thistle (CIRAR, *Cirsium arvense*), poinsettia (EPHHL, *Euphorbia heterophylla*), wild buckwheat (POLCO, *Polygonum convolvulus*), giant foxtail (SETFA, *Setaria faberi*), chickweed (STEME, *Stellaria media*), and wild pansy (VIOTR, *Viola tricolor*) was evaluated. The results are summarized in Tables 26-30.

TABLE 26

Effect (% visual injury) of compound 1 on corn/maize (ZEAMX).

| | | Application rate (g/ha) | | |
|---|---|---|---|---|
| | | compound 1 | 35 | 0 | 35 |
| | | isoxadifen-ethyl | 0 | 35 | 35 |
| ZEAMX | Obs | | 40 | 0 | 0 |
| | Exp | | — | — | 40 |
| | Δ | | | | −40 |
| ABUTH | Obs | | 85 | 0 | 85 |
| | Exp | | — | — | 85 |
| | Δ | | | | 0 |

TABLE 26-continued

Effect (% visual injury) of compound 1 on corn/maize (ZEAMX).

| | | Application rate (g/ha) | | |
|---|---|---|---|---|
| | compound 1 | 35 | 0 | 35 |
| | isoxadifen-ethyl | 0 | 35 | 35 |
| AMARE | Obs | 100 | 0 | 100 |
| | Exp | — | — | 100 |
| | Δ | | | 0 |
| BRSNW | Obs | 99 | 0 | 100 |
| | Exp | — | — | 99 |
| | Δ | | | 1 |
| POLCO | Obs | 99 | 0 | 100 |
| | Exp | — | — | 99 |
| | Δ | | | 2 |
| STEME | Obs | 100 | 0 | 100 |
| | Exp | — | — | 100 |
| | Δ | | | 0 |
| VIOTR | Obs | 64 | 0 | 70 |
| | Exp | — | — | 64 |
| | Δ | | | 6 | g/ha = grams per hectare
ZEAMX = *Zea mays* (corn/maize)
ABUTH = *Abutilon theophrasti* (velvetleaf)
AMARE = *Amaranthus retroflexus* (pigweed)
BRSNW = *Brassica napus* (winter rape)
POLCO = *Polygonum convolvulus* (wild buckwheat)
STEME = *Stellaria media* (chickweed)
VIOTR = *Viola tricolor* (wild pansy)

TABLE 27

Effect (% visual injury) of compound 2 on corn/maize (ZEAMX).

| | | Application rate (g/ha) | | |
|---|---|---|---|---|
| | compound 2 | 35 | 0 | 35 |
| | isoxadifen-ethyl | 0 | 35 | 35 |
| ZEAMX | Obs | 35 | 0 | 0 |
| | Exp | — | — | 35 |
| | Δ | | | −35 |
| AMARE | Obs | 100 | 0 | 100 |
| | Exp | — | — | 100 |
| | Δ | | | 0 |
| BRSNW | Obs | 100 | 0 | 100 |
| | Exp | — | — | 100 |
| | Δ | | | 0 |
| CHEAL | Obs | 97 | 0 | 100 |
| | Exp | — | — | 97 |
| | Δ | | | 3 |
| CIRAR | Obs | 70 | 0 | 85 |
| | Exp | — | — | 70 |
| | Δ | | | 15 |
| EPHHL | Obs | 100 | 0 | 100 |
| | Exp | — | — | 100 |
| | Δ | | | 0 |
| POLCO | Obs | 100 | 0 | 100 |
| | Exp | — | — | 100 |
| | Δ | | | 0 |
| STEME | Obs | 100 | 0 | 100 |
| | Exp | — | — | 100 |
| | Δ | | | 0 |
| VIOTR | Obs | 40 | 0 | 60 |
| | Exp | — | — | 40 |
| | Δ | | | 20 | g/ha = grams per hectare
ZEAMX = *Zea mays* (corn/maize)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
EPHHL = *Euphorbia heterophylla* (poinsettia)
POLCO = *Polygonum convolvulus* (wild buckwheat)
STEME = *Stellaria media* (chickweed)
VIOTR = *Viola tricolor* (wild pansy)

TABLE 28

Effect (% visual injury) of compound 4 on corn/maize (ZEAMX).

| | | Application rate (g/ha) | | |
|---|---|---|---|---|
| | compound 4 | 35 | 0 | 35 |
| | isoxadifen-ethyl | 0 | 35 | 35 |
| ZEAMX | Obs | 35 | 0 | 0 |
| | Exp | — | — | 35 |
| | Δ | | | −35 |
| ABUTH | Obs | 80 | 0 | 80 |
| | Exp | — | — | 80 |
| | Δ | | | 0 |
| AMARE | Obs | 100 | 0 | 100 |
| | Exp | — | — | 100 |
| | Δ | | | 0 |
| BRSNW | Obs | 97 | 0 | 100 |
| | Exp | — | — | 97 |
| | Δ | | | 3 |
| CHEAL | Obs | 97 | 0 | 97 |
| | Exp | — | — | 97 |
| | Δ | | | 0 |
| CIRAR | Obs | 75 | 0 | 93 |
| | Exp | — | — | 75 |
| | Δ | | | 18 |
| STEME | Obs | 93 | 0 | 95 |
| | Exp | — | — | 93 |
| | Δ | | | 2 | g/ha = grams per hectare
ZEAMX = *Zea mays* (corn/maize)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
STEME = *Stellaria media* (chickweed)

TABLE 29

Effect (% visual injury) of compound 5 on corn/maize (ZEAMX).

| | | Application rate (g/ha) | | |
|---|---|---|---|---|
| | compound 5 | 35 | 0 | 35 |
| | isoxadifen-ethyl | 0 | 35 | 35 |
| ZEAMX | Obs | 35 | 0 | 0 |
| | Exp | — | — | 35 |
| | Δ | | | −35 |
| ABUTH | Obs | 80 | 0 | 80 |
| | Exp | — | — | 80 |
| | Δ | | | 0 |
| AMARE | Obs | 100 | 0 | 100 |
| | Exp | — | — | 100 |
| | Δ | | | 0 |
| BRSNW | Obs | 97 | 0 | 100 |
| | Exp | — | — | 97 |
| | Δ | | | 3 |
| CHEAL | Obs | 100 | 0 | 100 |
| | Exp | — | — | 100 |
| | Δ | | | 0 |
| CIRAR | Obs | 80 | 0 | 85 |
| | Exp | — | — | 80 |
| | Δ | | | 5 |
| STEME | Obs | 85 | 0 | 100 |
| | Exp | — | — | 85 |
| | Δ | | | 15 |

TABLE 29-continued

Effect (% visual injury) of compound 5 on corn/maize (ZEAMX).

| | | Application rate (g/ha) | | |
|---|---|---|---|---|
| | | compound 5 | 35 | 0 | 35 |
| | | isoxadifen-ethyl | 0 | 35 | 35 |
| VIOTR | Obs | 40 | 0 | 70 |
| | Exp | — | — | 40 |
| | Δ | | | 30 | g/ha = grams per hectare
ZEAMX = *Zea mays* (corn/maize)
ABUTH = *Abutilon theophrasti* (velvetleaf)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
STEME = *Stellaria media* (chickweed)
VIOTR = *Viola tricolor* (wild pansy)

TABLE 30

Effect (% visual injury) of compound 6 on corn/maize (ZEAMX).

| | | Application rate (g/ha) | | |
|---|---|---|---|---|
| | | compound 6 | 35 | 0 | 35 |
| | | isoxadifen-ethyl | 0 | 35 | 35 |
| ZEAMX | Obs | 25 | 0 | 0 |
| | Exp | — | — | 25 |
| | Δ | | | −25 |
| AMARE | Obs | 100 | 0 | 100 |
| | Exp | — | — | 100 |
| | Δ | | | 0 |
| BRSNW | Obs | 75 | 0 | 95 |
| | Exp | — | — | 75 |
| | Δ | | | 20 |
| CHEAL | Obs | 100 | 0 | 100 |
| | Exp | — | — | 100 |
| | Δ | | | 0 |
| CIRAR | Obs | 75 | 0 | 80 |
| | Exp | — | — | 75 |
| | Δ | | | 5 |
| STEME | Obs | 97 | 0 | 100 |
| | Exp | — | — | 97 |
| | Δ | | | 3 |
| VIOTR | Obs | 30 | 0 | 80 |
| | Exp | — | — | 30 |
| | Δ | | | 50 |
| POLCO | Obs | 97 | 0 | 100 |
| | Exp | — | — | 97 |
| | Δ | | | 3 |
| SETFA | Obs | 10 | 0 | 60 |
| | Exp | — | — | 10 |
| | Δ | | | 50 | g/ha = grams per hectare
ZEAMX = *Zea mays* (corn/maize)
AMARE = *Amaranthus retroflexus* (pigweed)
BRSNW = *Brassica napus* (winter rape)
CHEAL = *Chenopodium album* (lambsquarters)
CIRAR = *Cirsium arvense* (thistle)
STEME = *Stellaria media* (chickweed)
VIOTR = *Viola tricolor* (wild pansy)
POLCO = *Polygonum convolvulus* (wild buckwheat)
SETFA = *Setaria faberi* (giant foxtail)

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A safened herbicidal composition, comprising:

(a) a pyridine carboxylic acid herbicide defined by Formula (I)

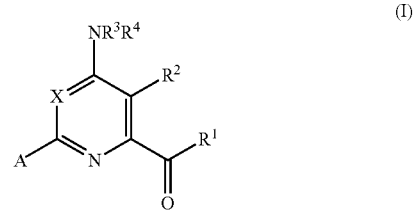

wherein

X is CY, wherein Y is halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$, wherein $R^{1'}$ is hydrogen, $C_1$-$C_8$ alkyl, $C_1$-$C_6$ haloalkyl, or $C_7$-$C_{10}$ arylalkyl;

$R^2$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, or cyano;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, or $C_1$-$C_6$ alkylsulfonyl, A is A15

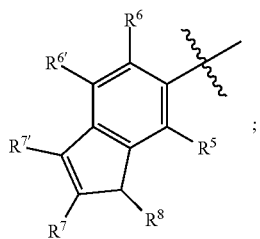

A15

$R^5$ is halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_1$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof; and (b) an azole carboxylate safener selected from the group consisting of fenchlorazole, isoxadifen, mefenpyr, agriculturally acceptable salts or esters thereof; and combinations thereof.

2. The composition of claim 1, wherein the pyridine carboxylic acid herbicide is a compound defined by Formula (II)

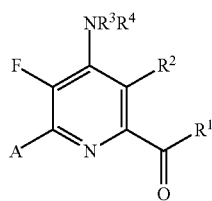

(II)

wherein
$R^1$ is $OR^{1'}$, wherein $R^{1'}$ is hydrogen, $C_1$-$C_8$ alkyl, $C_1$-$C_6$ haloalkyl, or $C_7$-$C_{10}$ arylalkyl;
$R^2$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, or cyano;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, or $C_1$-$C_6$ alkylsulfonyl;

A is A15;

$R^5$ is halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

3. The composition of claim 2, wherein
$R^1$ is $OR^{1'}$, wherein $R^{1'}$ is hydrogen, $C_1$-$C_8$ alkyl, or $C_7$-$C_{10}$ arylalkyl;

$R^2$ is halogen, $C_1$-$C_4$ alkyl, $C_1$-$C_4$ haloalkyl, $C_2$-$C_4$-alkenyl, $C_2$-$C_4$ haloalkenyl, $C_2$-$C_4$ alkynyl, $C_1$-$C_4$-alkoxy, $C_1$-$C_4$ haloalkoxy, $C_1$-$C_4$ alkylthio, or $C_1$-$C_4$ haloalkylthio;

$R^3$ and $R^4$ are hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, or $C_1$-$C_3$ haloalkylcarbonyl;

A is A15;

$R^5$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, or $C_2$-$C_4$ halo alkylamino;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, CN, or $NO_2$;

$R^7$ and $R^{7'}$ are independently hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, cyclopropyl, amino, or $C_1$-$C_4$ alkylamino; and $R^8$ is hydrogen, $C_1$-$C_6$ alkyl, $C_1$-$C_4$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, $C_1$-$C_6$ alkoxycarbonyl, or $C_1$-$C_6$ alkylcarbamyl.

4. The composition of claim 1, wherein the pyridine carboxylic acid herbicide is a compound defined by Formula (III):

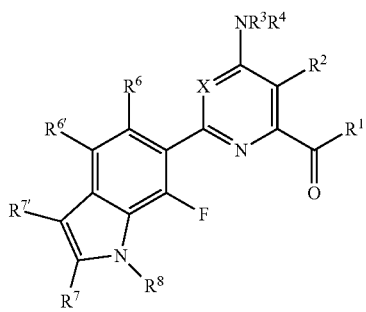

(III)

wherein
- X is CY, wherein Y is halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;
- $R^1$ is $OR^{1'}$, wherein $R^{1'}$ is hydrogen, $C_1$-$C_8$ alkyl, $C_1$-$C_6$ haloalkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;
- $R^2$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, or cyano;
- $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, or $C_1$-$C_6$ alkylsulfonyl;
- $R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, CN, or $NO_2$;
- $R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and
- $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

5. The composition of claim 1, wherein the pyridine carboxylic acid herbicide is one of the following:

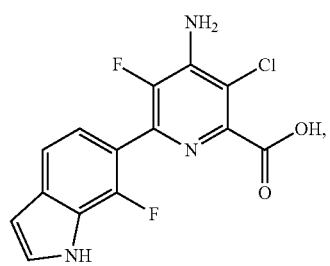

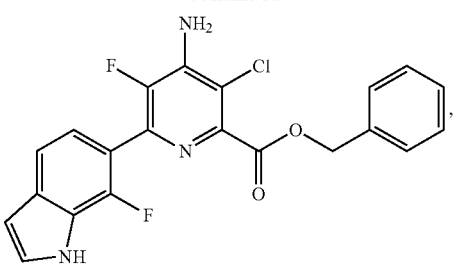

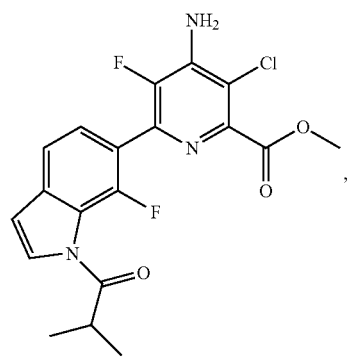

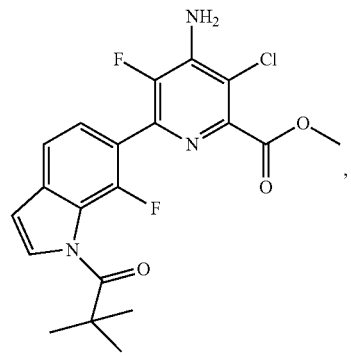

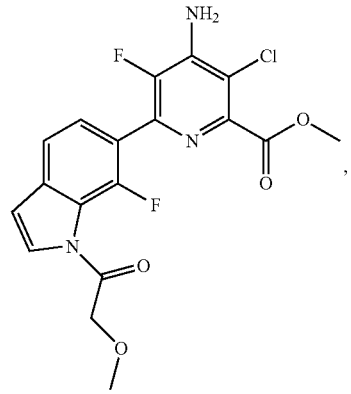

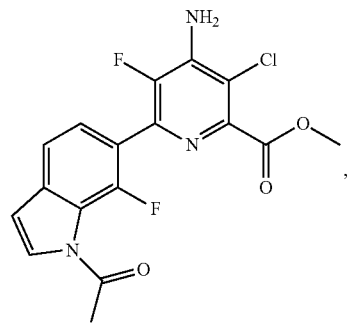

-continued

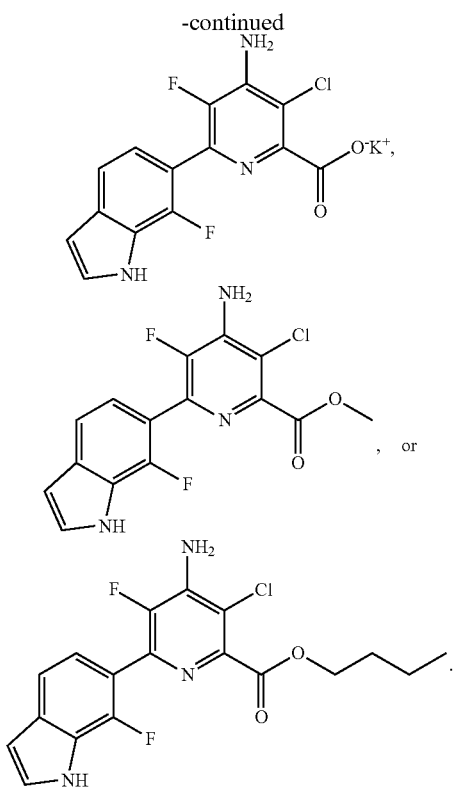

6. The composition of claim 1, wherein the pyridine carboxylic acid herbicide is

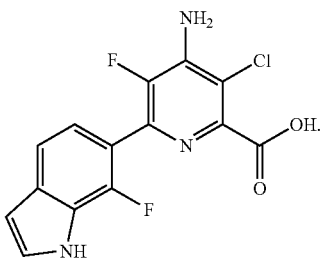 [SMILES: Nc1c(F)c(-c2ccc3cc[nH]c3c2F)nc(C(=O)O)c1Cl]

7. The composition of claim 1, wherein the weight ratio of (a) in g ae/ha to (b) in g ai/ha is from 65:1 to 1:5.

8. The composition of claim 1, further comprising an agriculturally acceptable adjuvant or carrier.

9. The composition of claim 1, further comprising an additional pesticide.

10. The composition of claim 1, wherein the active ingredients in the composition consist of (a) and (b).

11. A method of controlling undesirable vegetation, comprising applying to vegetation or an area adjacent the vegetation or applying to soil or water to control the emergence or growth of vegetation the composition of claim 1.

12. The method of claim 11, wherein (a) and (b) are applied post-emergence to the undesirable vegetation.

13. The method of claim 11, wherein (a) is applied in amount of from 0.1 g ae/ha to 300 g ae/ha.

14. The method of claim 11, wherein (b) is applied in amount of from 1 g ai/ha to 300 g ai/ha.

15. The method of claim 11, further comprising applying an additional pesticide.

16. The method of claim 11, wherein the undesirable vegetation is controlled in wheat, corn/maize, barley, triticale, rye, teff, oats, sorghum, rice, sugarcane, vineyards, orchards, perennial plantation crops, soybeans, cotton, sunflower, oilseed rape/canola, sugarbeets, turf, range and pasture, industrial vegetation management (IVM), rights-of-way, or combinations thereof.

17. The method of claim 11, wherein the undesirable vegetation is controlled in wheat, corn/maize, barley, tame oats, rice, or combinations thereof.

18. The method of claim 11, wherein the undesirable vegetation is controlled in a glyphosate-, glufosinate-, dicamba-, phenoxy auxin-, pyridyloxy auxin-, aryloxyphenoxypropionate-, acetyl CoA carboxylase (ACCase) inhibitor-, imidazolinone-, acetolactate synthase (ALS) inhibitor-, 4-hydroxyphenyl-pyruvate dioxygenase (HPPD) inhibitor-, protoporphyrinogen oxidase (PPO) inhibitor-, triazine-, or bromoxynil-tolerant crop.

19. The method of claim 18, wherein the tolerant crop is wheat, corn/maize, barley, tame oats, rice, or combinations thereof.

20. The method of claim 11, wherein the undesirable vegetation includes a broadleaf weed.

21. The method of claim 11, wherein the undesirable vegetation comprises a herbicide resistant or tolerant weed.

22. The method of claim 11, wherein the undesirable vegetation includes velvetleaf (ABUTH, *Abutilon theophrasti*), pigweed (AMARE, *Amaranthus retroflexus*), winter rape (BRSNW, *Brassica napus*), lambsquarters (CHEAL, *Chenopodium album*), thistle (CIRAR, *Cirsium arvense*), nutsedge (CYPES, *Cyperus esculentus*), poinsettia (EPHHL, *Euphorbia heterophylla*), wild buckwheat (POLCO, *Polygonum convolvulus*), giant foxtail (SETFA, *Setaria faberi*), sorghum (SORVU, *Sorghum bicolor*), chickweed (STEME, *Stellaria media*), wild pansy (VIOTR, *Viola tricolor*), or a combination thereof.

23. The method of claim 11, wherein the active ingredients applied to the vegetation or an area adjacent the vegetation or applied to soil or water to control the emergence or growth of vegetation consist of (a) and (b).

* * * * *

UNITED STATES PATENT AND TRADEMARK OFFICE
CERTIFICATE OF CORRECTION

PATENT NO.           : 9,526,244 B2                               Page 1 of 1
APPLICATION NO.      : 14/854172
DATED                : December 27, 2016
INVENTOR(S)          : Norbert M. Satchivi et al.

It is certified that error appears in the above-identified patent and that said Letters Patent is hereby corrected as shown below:

In the Claims

Amend claim to correct Formula A15 in Claim 1, Column 89, Line 5 of the issued patent to:

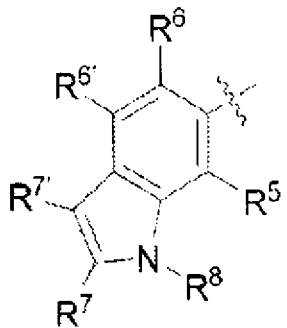

Signed and Sealed this
Twenty-fifth Day of April, 2017

Michelle K. Lee
*Director of the United States Patent and Trademark Office*